United States Patent [19]
Obendorf et al.

[11] Patent Number: 6,162,795
[45] Date of Patent: Dec. 19, 2000

[54] PREPARATION OF FAGOPYRITOLS AND USES THEREFOR

[75] Inventors: Ralph L. Obendorf, Ithaca, N.Y.; Marcin Horbowicz, Prusa, Poland

[73] Assignee: Cornell Research Foundation, Inc., Ithaca, N.Y.

[21] Appl. No.: 09/073,467

[22] Filed: May 6, 1998

Related U.S. Application Data

[60] Provisional application No. 60/045,927, May 7, 1997.

[51] Int. Cl.$^7$ .......................... A61K 31/70; C07H 15/22; C07H 3/04; C07H 3/06

[52] U.S. Cl. .................. 514/35; 514/25; 514/53; 514/61; 514/866; 536/4.1; 536/123.1; 536/123.13; 536/128

[58] Field of Search .................. 514/23, 25, 53, 514/61, 35, 866; 536/4.1, 120, 123.1, 123.13, 128

[56] References Cited

U.S. PATENT DOCUMENTS

| | | |
|---|---|---|
| 2,112,553 | 3/1938 | Bartow et al. . |
| 2,456,470 | 12/1948 | Thomas . |
| 3,270,064 | 8/1966 | Inaba et al. . |
| 4,010,258 | 3/1977 | Murao . |
| 4,482,761 | 11/1984 | Chao et al. . |
| 4,933,281 | 6/1990 | Daniels et al. . |
| 5,064,762 | 11/1991 | Rabinowitz . |
| 5,091,596 | 2/1992 | Kennington et al. . |
| 5,096,594 | 3/1992 | Rabinowitz . |
| 5,122,603 | 6/1992 | Larner et al. . |
| 5,124,360 | 6/1992 | Larner et al. . |
| 5,296,364 | 3/1994 | Agawal . |
| 5,317,095 | 5/1994 | Suzuki et al. . |
| 5,406,005 | 4/1995 | Piccariello . |
| 5,463,142 | 10/1995 | Riley et al. . |
| 5,516,950 | 5/1996 | Piccariello et al. . |
| 5,827,896 | 10/1998 | Ostlund et al. ............... 514/715 |

FOREIGN PATENT DOCUMENTS

| | | |
|---|---|---|
| 3-11026 | 1/1991 | Japan . |

OTHER PUBLICATIONS

Yasui, "Dissimilarity in Low Molecular Weight Carbohydrate Composition of the Seeds of Cultivated Soybean [*Glycine max* (L.) Merrill subsp. *max*]and Wild Soybean [*G. max* subsp. *soja* (SIEB. et ZUCC.)Ohashi]," *Agric. Biol. Chem.*, 49:933–937 (1985).

Quemener et al., "Ciceritol, a Pinitol Digalactoside from Seeds of Chickpea, Lentil and White Lupin," *Phytochemistry*, 22:1745–1751 (1983).

Obendorf et al., "Seed Desiccation Tolerance and Storability: Dependence on the Flatulence–Producing Sugars," International Workshop: Desiccation Tolerance and Sensitivity of Seeds and Vegetative Plant Tissues, South Africa, Jan. 19, 1994 (Abstract of Oral Presentation).

Obendorf, "Seed Set and Cessation of Seed Growth in Buckwheat," Developing a Strategic Plan for Integrated Buckwheat Research, North Dakota State University Research and Extension Center, Jul. 21, 1994, (Abstract of Oral Presentation).

Obendorf et al., "Seed Set and Cessation of Seed Growth in Buckwheat," Quarterly Report to Sponsors, Apr. 1–Jun. 30, 1994.

Obendorf, "Buckwheat Pharmaceuticals: 1. Characterization," "Buckwheat Pharmaceuticals: 2. Model for Industrial Isolation," "Buckwheat Pharmaceuticals: 3. Equipment," Research Proposals to MINN–DAK Growers Ltd., Nov. 27, 1995.

Ogawa et al., "A new glycoside, 1D–2–O–alpha–D–galactopyranosyl–chiro–inositol from jojoba beans", Carbohydrate Research, vol. 302: 219–221, 1997.

Schweizer et al., "Low Molecular Weight Carbohydrates From Leguminous Seeds; A New Disaccharide: Galactopinitol," *J. Sci. Fd Agric.*, 29:148–154 (1978).

Schweizer et al., "Purification and Structure Determination of Three α–D–galactopyranosylcyclitols From Soya Bean," *Carbo. Res.*, 95:61–71 (1981).

Shiomi et al., "A New Digalactosyl Cyclitol From Seed Balls of Sugar Beet," *Agric. Biol. Chem.*, 52:1587–1588 (1988).

Ortmeyer et al., "In vivo D–chiroinositol Activates Skeletal Muscle Glycogen Synthase and Inactivates Glycogen Phosphorylase in Rhesus Monkeys," *Nutritional Biochemistry*, 6:499–503 (1995).

Ortmeyer et al., "Effects of D–Chiroinositol Added to a Meal on Plasma Glucose and Insulin In Hyperinsulinemic Rhesus Monkeys," *Obesity Res.* 3 (Supp 4):605S–608S (1995).

Horbowicz et al., "Maturing Buckwheat Seeds Accumulate Galacto–chiro–inositol Instead of Stachyose," Abstract 908, *Plant Physiology*, 105:S–164 (1994).

Horbowicz et al., "Galactosyl–chiro–inositol in Buckwheat Seeds Correlates with Desiccation Tolerance During Maturation and Germination," *Agronomy Abst.*, 178, (1994).

Horbowicz et al., "Fagopyritol B1, O–α–D–galactopyranosyl–(1→2)–D–chiro–inositol, a Galactosyl Cyclitol in Maturing Buckwheat Seeds Associated with Desiccation Tolerance," *Planta*, 205:1–11 (1998).

Szczecinski et al., "NMR Investigation of the Structure of Fagopyritol B1 from Buckwheat Seeds," *Bulletin of the Polish Academy of Sciences Chemistry*, 46(1):9–13 (1998).

*Primary Examiner*—Howard C. Lee
*Attorney, Agent, or Firm*—Nixon Peabody LLP

[57] ABSTRACT

The present invention describes isolated Fagopyritol A1, isolated Fagopyritol A2, and isolated Fagopyritol B3. Compositions which include two or more of Fagopyritol A1, Fagopyritol A2, Fagopyritol B1, Fagopyritol B2, Fagopyritol B3, and D-chiro-inositol, at least one of which is an isolated Fagopyritol A1, isolated Fagopyritol A2, or isolated Fagopyritol B3, are also disclosed. Methods for preparing substantially pure Fagopyritol A1, Fagopyritol A2, Fagopyritol B1, Fagopyritol B2, Fagopyritol B3, or mixtures thereof from buckwheat are also described. The fagopyritols can be used to prepare pharmaceutical compositions, the administration of which can be used to treat diabetes.

25 Claims, 13 Drawing Sheets

PREPARATION OF FAGOPYRITOLS AND USES THEREFOR

This application claims the benefit of U.S. Provisional Patent Application Serial No. 60/045,927, filed May 7, 1997, which is hereby incorporated by reference.

FIELD OF THE INVENTION

The present invention relates to fagopyritols and to methods for using fagopyritols.

BACKGROUND OF THE INVENTION

Diabetes mellitus is a major global health problem which is recognized by the World Health Organization to be reaching epidemic proportions. It is now the fourth leading cause of death in most developed countries and a disease that is increasing rapidly in countries undergoing industrialization. Estimates of worldwide diabetes prevalence have increased from 30 million in 1985 to more than 100 million in 1994. Diabetes mellitus is a disease caused by defective carbohydrate metabolism and characterized by abnormally large amounts of glucose in the blood and urine. Diabetes mellitus can eventually damage the eyes, kidneys, heart, and limbs, and can endanger pregnancy.

Diabetes mellitus is usually classified into two types. Type I, or insulin-dependent diabetes mellitus ("IDDM"), formerly called juvenile-onset diabetes because it occurs primarily in children and young adults, has been implicated as one of the autoimmune diseases. Rapid in onset and progress, it accounts for about 10 to 15 percent of all cases. Type II, or non-insulin-dependent diabetes mellitus ("NIDDM"), formerly called adult-onset diabetes, is usually found in persons over 40 years old and progresses slowly. Often it is not accompanied by clinical illness in its initial stages and is detected instead by elevated blood or urine glucose levels.

Diabetes is considered a group of disorders with multiple causes, rather than a single disorder. The human pancreas secretes a hormone called insulin that facilitates the entry of glucose into tissues of the body and its utilization, thus providing energy for bodily activities. In a person with diabetes, however, the entry of glucose is impaired, a result either of a deficiency in the amount of insulin produced or of altered target cells. Consequently, sugar builds up in the blood and is excreted in the urine. In the Type I diabetic, the problem is almost always a severe or total reduction in insulin production. In the Type II diabetic, the pancreas often makes a considerable quantity of insulin, but the hormone is unable to promote the utilization of glucose by tissues.

With adequate treatment most diabetics maintain blood-sugar levels within a normal or nearly normal range. This permits them to live normal lives and prevents some long-term consequences of the disease. For the Type I diabetic with little or no insulin production, therapy involves insulin injections. For Type II diabetics, most of whom are at least moderately overweight, therapy is based on diet control, weight reduction, and exercise. Weight reduction appears partially to reverse the condition of insulin resistance in the tissues. If a Type II patient's blood-sugar level is still high, the physician may add insulin injections to the treatment regimen. In many cases, the need for insulin injections is not due to a deficiency in insulin but, instead, due to the patient's reduced ability to utilize insulin efficiently because of a deficiency of galactosamine D-chiro-inositol, an insulin mediator.

Besides the discomfort associated with its administration by injection, the problem of controlling the dose of insulin also exists. The hypoglycemia produced by an insulin overdose may lead to tremors, cold sweat, piloerection, hypothermia, and headache, accompanied by confusion, hallucinations, bizarre behavior, and, ultimately, convulsions and coma. Therefore, it would be advantageous to control a diabetic's blood-sugar level without resort to insulin injections. The present invention is directed to providing such control.

SUMMARY OF THE INVENTION

The present invention relates to an isolated Fagopyritol A1, an isolated Fagopyritol A2, and an isolated Fagopyritol B3.

The present invention is also directed to a composition comprising two or more of Fagopyritol A1, Fagopyritol A2, Fagopyritol B1, Fagopyritol B2, Fagopyritol B3, and D-chiro-inositol. The composition comprises at least one isolated Fagopyritol A1, isolated Fagopyritol A2, or isolated Fagopyritol B3.

The present invention also relates to a substantially pure fagopyritol selected from the group consisting of Fagopyritol A1, Fagopyritol A2, Fagopyritol B1, Fagopyritol B2, and Fagopyritol B3.

In another aspect, the present invention relates to a method for preparing a material selected from the group consisting of Fagopyritol A1, Fagopyritol A2, Fagopyritol B1, Fagopyritol B2, Fagopyritol B3, and a mixture thereof. Buckwheat is contacted with a solvent under conditions effective to produce a crude extract. The crude extract contains non-fagopyritol materials and one or more fagopyritols selected from the group consisting of Fagopyritol A1, Fagopyritol A2, Fagopyritol B1, Fagopyritol B2, and Fagopyritol B3. The non-fagopyritol materials are then separated from the one or more fagopyritols.

The isolated fagopyritols of the present invention can be used in a pharmaceutical composition which also includes a pharmaceutical carrier. This pharmaceutical composition or, alternatively, the substantially pure fagopyritols of the present invention or the isolated fagopyritols of the present invention can be administered to a patient to treat diabetes.

BRIEF DESCRIPTION OF THE DRAWINGS

FIG. 1A is a vertical section through a mature buckwheat achene. FIG. 1B is a horizontal cross section of a mature buckwheat achene. FIG. 1C is a horizontal cross section of a mature buckwheat groat (dehulled buckwheat achene). FIG. 1D is a horizontal cross section of a mature buckwheat groat showing its milling fractions and fracture planes.

FIG. 3A is a gas chromatogram before hydrolysis; FIG. 3B is a gas chromatogram after hydrolysis with α-galactosidase enzyme for 23 h; and FIG. 3C is a gas chromatogram after acid hydrolysis with 2 N trifluoroacetic acid ("TFA") at 70° C. for 3 h. The peaks are identified as follows: (a) D-chiro-inositol, (b) myo-inositol, (c) phenyl α-D-glucoside (internal standard), (d) sucrose, (e) Fagopyritol A1, (f) Fagopyritol B1, (g) galactinol, (k) Fagopyritol A2, (l) Fagopyritol B2, (1) galactose, (2) glucose, and (3) fructose. Trimethylsilyl ("TMS") derivatives of glucose, fructose, and galactose capture the anomeric forms of the sugars as distinct TMS products.

FIG. 7A shows the desiccation tolerance (●) and d to 50% germination (○) as a function of d during slow drying. FIG. 7B shows amount of cyclitols D-chiro-inositol (●) and myo-inositol (■) per embryo as a function of d during slow drying. FIG. 7C shows the amount of galactosyl cyclitols Fagopyritol B1 (●), Fagopyritol A1 (filled triangle), and galactinol (■) per embryo as a function of d during slow drying. FIG. 7D shows the amount of digalactosyl cyclitols Fagopyritol B2 (●), Fagopyritol A2 (filled triangle), and digalactosyl myo-inositol (□) per embryo as a function of d during slow drying. FIG. 7E shows the amount of sucrose (●) as a function of d during slow drying.

FIG. 8A shows the desiccation tolerance (●) and d to 50% germination (○) as a function of d at high relative humidity. FIG. 8B shows the amount of cyclitols D-chiro-inositol (●) and myo-inositol (■) per embryo as a function of d at high relative humidity. FIG. 8C shows the amount of galactosyl cyclitols Fagopyritol B1 (●), Fagopyritol A1 (filled triangle), and galactinol (■) per embryo as a function of d at high relative humidity. FIG. 8D shows the amount of digalactosyl and trigalactosyl cyclitols Fagopyritol A2 (filled triangle), Fagopyritol B2 (●), Fagopyritol B3 (○), and digalactosyl myo-inositol (□) per embryo as a function of d at high relative humidity. FIG. 8E shows the amount of sucrose (●) per embryo as a function of d at high relative humidity.

FIG. 9A shows the desiccation tolerance (●) and onset of germination (○) as a function of h of germination on wet paper towels at 25° C. FIG. 9B shows the axis length (●) as a function of h of germination on wet paper towels at 25° C. FIG. 9C shows the amount of cyclitols D-chiro-inositol (●) and myo-inositol (○) per axis as a function of h of germination on wet paper towels at 25° C. FIG. 9D shows the amount of cyclitols D-chiro-inositol (●) and myo-inositol (○) per cotyledon as a function of h of germination on wet paper towels at 25° C. FIG. 9E shows the amount of Fagopyritol B1 (●), Fagopyritol A1 (○), Fagopyritol B2 (■), and Fagopyritol A2 (□) per axis as a function of h of germination on wet paper towels at 25° C. FIG. 9F shows the amount of Fagopyritol B1 (●), Fagopyritol A1 (○), Fagopyritol B2 (■), and Fagopyritol A2 (□) per cotyledon as a function of h of germination on wet paper towels at 25° C. FIG. 9G shows the amount of sucrose (●) per axis as a function of h of germination on wet paper towels at 25° C. FIG. 9H shows the amount of sucrose (●) per cotyledon as a function of h of germination on wet paper towels at 25° C. FIG. 9I shows the amount of glucose (●), fructose (○), and unknown (■) per axis as a function of h of germination on wet paper towels at 25° C. FIG. 9J shows the amount of maltose (●), maltotriose (○), and maltotetraose (■) per cotyledon as a function of h of germination on wet paper towels at 25° C.

DETAILED DESCRIPTION OF THE INVENTION

Figure 1A:
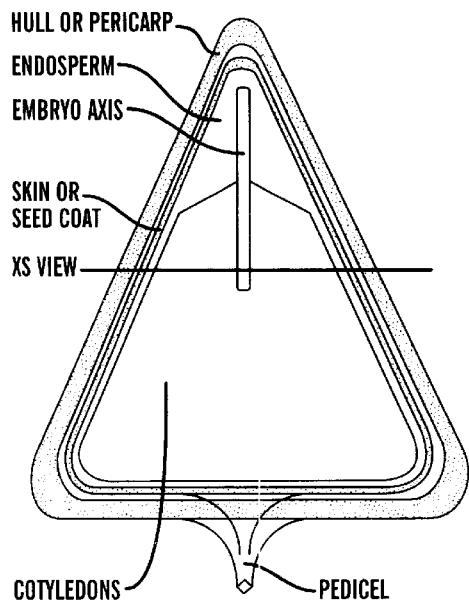
FIGS. 1A–1D are schematic diagrams showing the components of a buckwheat seed.

The present invention relates to fagopyritols. Fagopyritol is a general term used herein to mean an unspecified α-galactosyl D-chiro-inositol or its salt or derivative. More particularly, the present invention relates to isolated Fagopyritol A1, particularly Fagopyritol A1s have the following Formula I:

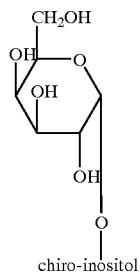
chiro-inositol and salts thereof.

The present invention also relates to an isolated Fagopyritol A2, particularly Fagopyritol A2s have the following Formula II:

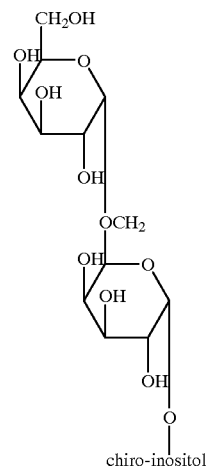
chiro-inositol and salts thereof.

The present invention further relates to an isolated Fagopyritol B3, particularly Fagopyritol B3s have the following Formula III:

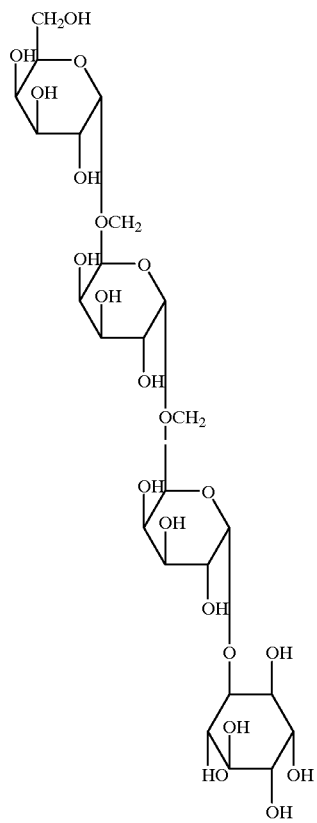

and salts and derivatives thereof.

Salts of the Fagopyritol A1s, A2s, and B3s of the present invention can be the reaction product of a base having a pKa (i.e., −log Ka) greater than the pKa of one or more of the fagopyritols→ hydroxyl groups, such as a metal hydroxide of alkoxide, an amonium hydroxide, or an amine (e.g. a tertiary amine, like triethyl amine). Exemplary salts are alkali metal salts, such as lithium salts, sodium salts, and potassium salts, alkali earth metal salts, such as calcium salts and barium salts, ammonium salts, sufonium salts, and phosphonium salts.

Derivatives of the Fagopyritol A1s, A2s, and B3s of the present invention include, for example, the reaction products of the fagopyritols with compounds bearing a carbon having a positive charge, such as an alkyl halide, in which case the derivative is an ether of the fagopyritol, or a carboxylic acid halide (e.g., acetyl chloride) or anhydride (e.g., acetic anhydride), in which case the derivative is an ester of the fagopyritol (e.g., the acetate).

As used herein, an isolated fagopyritol is one which is substantially free of other buckwheat components with which it naturally occurs. It is to be understood that the isolated fagopyritols of the present invention can be prepared by a variety of methods including, for example, by extraction from buckwheat or other natural sources, as well as by chemical synthesis.

The present invention also relates to substantially pure Fagopyritol A1, substantially pure Fagopyritol A2, and substantially pure Fagopyritol B3, preferably having Formula I, II, and III, respectively, their salts and derivatives. The present invention further relates to substantially pure Fagopyritol B1, particularly fagopyritols having the following Formula IV:

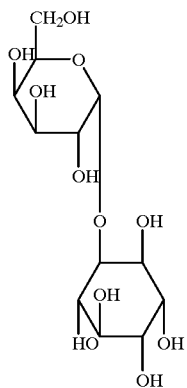

and their salts and derivatives. The present invention also relates to substantially pure Fagopyritol B2, particularly fagopyritols having the following Formula V:

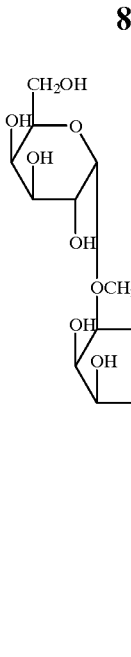

as well as their salts and derivatives. As referred to herein, substantially pure means substantially free of other compounds or materials, such as galactinol, myo-inositol, digalactosyl myo-inositol, phytin, aromatic materials (e.g. polyphenols and pigments and other colored aromatic materials), cell wall particles, proteins, and acids (e.g. organic acids, nucleic acids, and amino acids) and their salts. Typically, substantially pure fagopyritols are those having greater than about 95% purity, such as greater than about 98% purity or from about 95% to about 99% purity.

As indicated above, the fagopyritols of the present invention are not limited by their method of preparation. One particularly preferred method, involves purification of the subject fagopyritols from buckwheat. Briefly, buckwheat is contacted with a solvent under conditions effective to produce a crude extract containing non-fagopyritol materials and one or more fagopyritols selected from the group consisting of Fagopyritol A1, Fagopyritol A2, Fagopyritol B1, Fagopyritol B2, and Fagopyritol B3. The one or more fagopyritols are then separated from the non-fagopyritol materials. This process is described in greater detail below.

Any portion of the buckwheat plant (*Fagopyrum esculentum*) can be used in preparing the fagopyritols of the present invention.

The structure of developing buckwheat seeds has been reviewed and illustrated by Obendorf et al., "Structure and Chemical Composition of Developing Buckwheat Seed," pp. 244–251 in Janick et al., eds., *New Crops*, New York-:John Wiley & Sons (1993) ("Obendorf"), which is hereby incorporated by reference. Photographs of mature buckwheat seeds have been illustrated in reviews by Marshall et al., "Buckwheat: Description, Breeding, Production, and Utilization," *Advances in Cereal Science and Technology*, 5:157–210 (1982) ("Marshall") and Pomeranz, "Buckwheat: Structure, Composition, and Utilization," *CRC Critical Reviews in Food Science and Nutrition*, 19:213–258 (1983), which are hereby incorporated by reference. Most of the structural information in the latter reviews originated from a study of the scanning electron microscopy of the buckwheat kernel by Pomeranz et al., "Scanning Electron Microscopy of the Buckwheat Kernel," *Cereal Chemistry*, 49:23–25 (1972), which is hereby incorporated by reference. The embryo is positioned with the radicle (root) of the embryo at the pointed top of the buckwheat achene (the name of the mature buckwheat fruit) as shown schematically in FIG. 1A. As described by Obendorf, which is hereby incorporated by reference, the cotyledons have extended through the soft (mostly liquid) endosperm to reach the bottom of the endosperm by 8 days after pollination. The achene is attached to the raceme (name of inflorescence or flower cluster) of the mother plant by the pedicel. The embryo, including the axis and cotyledons continues to grow through the endosperm, curling around the margins of the endosperm and reaching the maximum dry weight at 16 days after pollination. The endosperm continues to accumulate dry matter (mostly starch) until 24 to 28 days after pollination. After a few more days the buckwheat grain (achene or fruit) is mature and dry.

Figure 1B:
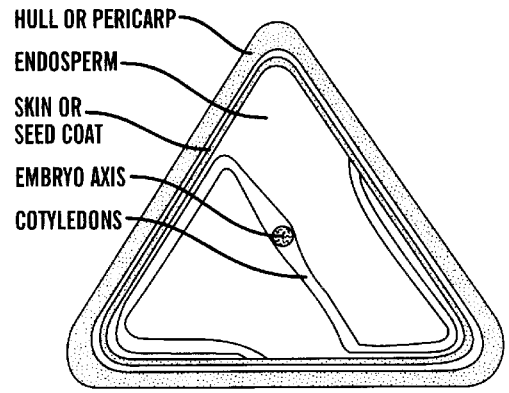
Figure 1C:
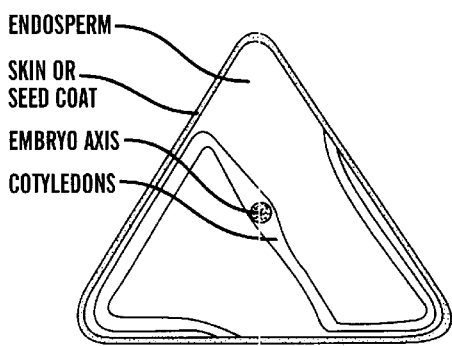

A horizontal cross-section view (see line marked "xs view" in FIG. 1A) of the mature buckwheat achene is schematically illustrated in FIG. 1B. This "top-down" view illustrates the hull (pericarp, fruit coat) as the outer layer of the achene (black with light cross-hatch markings in FIGS. 1B and 1C). The hull is a hard fibrous structure that is usually black or dark brown in color. The hull is the first layer to be removed during milling to produce dehulled groats (the true "seed" without the pericarp) (FIG. 1C). The outer part of the dehulled groat is the "skin" or seed coat (also called testa). This is a fibrous layer composed of seed coat cells with thickened cell walls and remnants of the nucellus (perisperm; 1–3 cells thick). The outermost layer of cells in the endosperm is called the aleurone layer and usually adheres to the seed coat and nucellus tissues in mature grains. The aleurone is a single layer of small cells that have thicker cell walls than those of the central endosperm cells, do not contain starch, and remain "alive" upon drying of the seed. The remainder of endosperm cells have thinner cell walls and are packed with starch granules as illustrated in Marshall, which is hereby incorporated by reference.

The buckwheat embryo has an axis (circle in center) and two thin, leaf-like cotyledons that wind through the endosperm to the margin and then bend to continue along the outer part of the endosperm near the seed coat (FIGS. 1B and 1C; embryo structures in black, endosperm structures in white, and seed coat or "skin" in shaded gray). In the mature grain, the cotyledons nearly surround the endosperm. The embryo (axis plus cotyledons) remain alive in the mature dry grain. After germination, the embryo forms the buckwheat seedling. In mature dry grain, the embryo and aleurone layer cells contain all of the fagopyritols and D-chiro-inositol in the buckwheat grain. The embryo (as well as the aleurone layer) contains most of the protein and nearly all of the oil, phytin, minerals, vitamins, and rutin, but only traces of starch. Nearly all of the starch is in the endosperm, but there is no starch in the aleurone layer, the outer most layer of the endosperm.

Figure 1D:
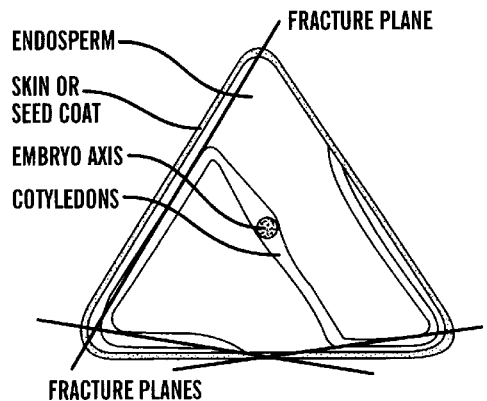

Whole groat flour contains the entire groat (FIG. 1C) ground without separation of fractions. Because of the fibrous nature of the seed coat, larger fragments usually form during milling of buckwheat groats. The fracture plane is usually inside the layers with thick-walled cells. Likewise in wheat, oats, and barley dry milling, the bran fraction contains the pericarp (with seed coat), nucellar remnants, aleurone, and subaleurone layers. The fracture plane is between the thicker-walled subaleurone layer and the thinner-walled central endosperm in these grains. Similarly, the aleurone layer of buckwheat usually adheres to the "bran" or "skins" fraction during milling. In the bran fraction, the "seed coat" (also known as testa), or "skin" adheres to the outer of the two cotyledons, and that part of the cotyledon tears off and separates with the bran fraction (see schematic illustration of theoretical fracture planes in FIG. 1D). Not all skins have adhering cotyledon tissues. Most of the endosperm has soft thin-walled cells that form flour during milling. In some seeds, the cotyledons in the center of the endosperm are quite loose and may flake off in larger segments of "pure" cotyledon tissue. These larger fragments of the cotyledons and axis may separate into the bran fraction also, but much of the soft embryo tissue is pulverized and separates with the light flour fraction that is rich in starch. For these reasons, the bran fractions can be rich sources of fagopyritols and D-chiro-inositol. Likewise, the light flour fraction contains fagopyritols from embryo fragments embedded in the endosperm, but the concentration is reduced due to dilution with large amounts of starch. Since the embryo matures before the endosperm, embryo size varies less than endosperm size in mature grain. In smaller seeds (less endosperm), the cotyledons are in contact with more of the seed coat while in larger seeds (more endosperm) the cotyledons are in contact with less of the total seed coats. "Purified bran" without hulls in the fraction, are rich in fagopyritols, minerals, protein, and oil.

Important to this description is that the embryo cells (cotyledons and axis) and the cells of the aleurone layer are the cells that contain sucrose, fagopyritols, rutin, phytin, most of the minerals, most of the vitamins, nearly all of the oil, and a high concentration of protein. Cells of the embryo and aleurone layer are "living" cells in the dry seed, but cells of the subaleurone, central endosperm, and seedcoat (testa or skin) are dead. Cells of the hull (pericarp) also are dead in a dry seed. Thus, any fraction that is rich in embryo and aleurone layer cells will be rich in these components. The central endosperm cells are predominantly starch, and, therefore, the light flour fraction is rich in starch. However, because the embryo traverses the central endosperm, much of the embryo breaks into small fragments and ends up in the light flour fraction, but more would be in the dark flour fraction (includes the skins, too) or in whole groat flour.

Preferred portions of the buckwheat plant for use in preparing the fagopyritols of the present invention are the buckwheat embryo, especially the embryonic axis, or any milling fraction rich in embryo, cotyledon, axis, or aleurone layer cells including "bran" or "purified bran" milling fractions. Because of its ready availability, it has been found that buckwheat flour, such as commercial fancy buckwheat flour (preferably having about 12.3% moisture) or whole groat flour prepared from commercial whole white groats, is an excellent source of buckwheat for the isolation of fagopyritols. Alternatively, the flour can be produced from buckwheat seeds, preferably dehulled buckwheat seeds. Irrespective of the buckwheat source, extraction is improved when the buckwheat, such as buckwheat flour, is ground to a fine powder, preferably to a powder which passes through a 100-mesh sieve. The buckwheat flour can be raw or defatted, defatting being effected by mixing the raw buckwheat with a solvent for fatty acids, such as alkane solvents, preferably hexanes. Although defatting increases the efficiency of the initial extraction steps, subsequent filtration and chromatography are generally more difficult when employing defatted flour.

The flour is then extracted with a suitable solvent. Suitable solvents for the extraction process include water, alcohol, and water/alcohol mixtures. Water extracts typically contain more suspended materials, probably because of the higher solubility of proteins and starch in water. Alcohol and alcohol/water extracts generally contain less suspended materials and also minimize microbial and endogenous enzyme activities during extraction. Suitable alcohols for use in alcohol and alcohol/water extraction include methanol, ethanol, isopropanol, and n-propanol, ethanol being preferred. Water/ethanol mixtures are the preferred extraction solvents. Of these, the preferred solvent mixtures are those where the ethanol-to-water volume ratio is from about 1:2 to about 2:1, more preferably about 1:1.

Extraction is carried out by mixing a suitable quantity of the extraction solvent with the buckwheat flour or other buckwheat source, preferably with agitation. Agitation can be effected with any suitable means, such as with a blender, preferably having a "high shear" polytron head, a paddle mixer, or a shearing mixer. When a blender is used as the agitation apparatus, good results are obtained when the blender is cycled 10 seconds on and then 10 seconds off for 1 or 2 min. The volume of the extraction solvent used per unit weight of flour is not particularly critical to the practice of the present invention. Typically, solvent/flour ratios (ml/g) of from about 1:1 to about 200:1 are suitable, with solvent/flour ratios of from about 10:1 to about 50:1 being preferred, and solvent/flour ratios of about 20:1 being most preferred.

The temperature at which the extraction is carried out is not particularly critical to the practice of the present invention. However, after hot extraction, the mixture can be too thick (due to swelling of starch present in the buckwheat) to filter or centrifuge efficiently, resulting in low volumes of extracted fagopyritols. Cold extraction at temperatures from about 4° C. to about room temperature (approximately 25° C.), preferably from about 10° C. to about room temperature, and most preferably at about room temperature generally produces the highest yields.

The duration of the extraction process depends on a number of factors, including the type and vigorousness of agitation, the shape of the container in which extraction is carried out, the solvent-to-flour ratio, the temperature at which the extraction process is carried out, the volume of the material being extracted, the fineness of the grinding (particle size) of the material being extracted, and the like. Preferably, extraction is carried out for a period of time sufficient to produce a homogeneous material. Typically, about 15 seconds to about 1 hour, preferably from about 1 to about 5 minutes, more preferably from about 1 to about 2 minutes is effective.

The yield of extracted fagopyritols can frequently be increased by repeating the extraction process one, two, or more times. Typically, on the first extraction, between 85 and 95% of the fagopyritols present are extracted. The second extraction, when performed, yields an additional 8–10%, and the third extraction generally produces yet an additional 1%.

After the first and optional additional extraction steps, the homogenate is permitted to settle, and the solvent is removed. Although solvent removal can be achieved by any suitable means, filtration, particularly ultrafiltration, or centrifugation yields the best results. The crude extract (e.g., the supernatant after centrifugation or the filtrate after filtration) is then preferably heated to a temperature sufficient to inactivate any alpha-galactosidase and/or other enzymes present in the buckwheat that may hydrolyze the fagopyritols. Generally, deactivation can be effected by heating the crude extract to a temperature of from about 70 to about 90° C., preferably about 80° C. After cooling, the crude extract is preferably clarified by filtration, concentrated by evaporation, and then further clarified by ultrafiltration. The composition of the crude extract can be monitored during the extraction process and subsequent filtration, centrifilgation, deactivation, evaporation, or clarification, by standard methods, including gas-liquid chromatography, high performance liquid chromatography ("HPLC"), spectrophotometric analysis, dye-binding protein assays, and atomic absorption analysis. If necessary, the enriched fraction of fagopyritols can be fractionated by ethanol precipitation to remove unwanted soluble carbohydrates of higher oligomeric forms (e.g., pentasaccharides and higher).

Recovery of the fagopyritols can be further enhanced by removing cell wall particles and large proteins, for example, by passing the crude extract through a filter having a cut off of from about 5000 $M_r$ to about 20,000 $M_r$, preferably about 10,000 $M_r$.

Additionally or alternatively, the fagopyritols can be further purified by removing non-carbohydrate contaminants with, for example, food-grade ion exchange resins, such as Syburn Resin (available from Aftech, Inc., Rochester, N.Y.), polyvinylpolypyrrolidone, ("PVPP") (e.g., Polyclar-VT, available from ISP Technologies, Inc., Wayne, N.J.), bentonite (e.g., KWK Bentonite agglomerated powder, available from Presque Isle Wine Cellars, North East, Pa.), and diatomaceous earth powder (available, e.g., from Celite Corporation, Lamoc, Calif.). Illustratively, charged materials can be removed from the crude extract, by passing the crude extract through an ion exchange material, such as Amberlite IRA-94 ion exchange resin and Dowex 50WX4 ion exchange resin (both available commercially from Sigma Chemical Company, St. Louis). Further purification of the fagopyritols can be effected by removing aromatic materials, such as polyphenolic materials, aromatic pigments, and other brown-colored contaminants, by passing the crude extract through a column containing a material which absorbs aromatic materials, such as polyvinylpyrrolidone ("PVP") or activated charcoal. The fagopyritols can then be precipitated by chilling the concentrated crude extract or by adding an alcohol, such as ethanol, to the concentrated extract, or both.

The resulting mixture of fagopyritols and other sugars can then be separated into its component fagopyritols, for example, chromatographically. For example, chromatographic separation can be carried out on an amine functionalized silica gel or by using a carbon-celite column or both. Generally, the carbon-celite column is better at removing water-soluble low-molecular-weight colored contaminants.

The preferred amine functionalized silica gel, 3-aminopropyl-functionalized silica gel, is available commercially from Sigma-Aldrich (Milwaukee, Wis.). The degree of functionalization of the silica gel is not critical to the practice of the present invention. Preferably, this silica gel is from about 5% to about 15% functionalized, and, more preferably, it is about 9% functionalized. Suitable solvents for loading the crude extract on and eluting the various fagopyritols from the 3-aminopropyl-functionalized silica gel can be readily ascertained by those skilled in the art. Preferably, the separation is carried out using an acetonitrile/water eluent. More preferably, the crude extract is loaded as an acetonitrile:water (70:30, v:v) solution and is eluted, stepwise, with 70:30 (v:v) acetonitrile:water, 60:40 (v:v) acetonitrile:water, and then 50:50 (v:v) acetonitrile:water. Subsequent to elution, the 3-aminopropyl functionalized silica gel can be regenerated by with 60:40 (v:v) acetonitrile:water. Generally, the order of elution when using a 3-aminopropyl-functionalized silica gel is as follows: monosaccharides, D-chiro-inositol, myo-inositol, sucrose, trehalose, Fagopyritol A1, Fagopritol B1, galactinol, Fagopyritol A2, Fagopritol B2, di-galactosyl myo-inositol, and Fagopyritol B3.

When a celite-carbon column is employed to effect chromatographic separation, suitable columns include those which contain a mixture of carbon (e.g., Darco-G60, J. T. Baker, Phillipsburg, N.J.) and celite (e.g., Celite 545-AW, Spelco, Bellefonte, Pa.). Generally, the column material is prepared by slurrying the carbon and celite in distilled water. The slurry is then packed into a suitably sized column, and the packed column is then washed with distilled water. The crude extract can be loaded using any suitable solvent, water being preferred. The carbon-celite column can be eluted with, for example, water, alcohol (e.g., ethanol), or combinations thereof Illustratively, elution can be carried out using 50% ethanol (i.e., a 50:50 (v/v) mixture of ethanol and water). Alteratively, the elution can be carried out stepwise, first eluting with distilled water, and then eluting with a series of mixtures of ethanol and water having increasing ethanol content. For example, the column can be first eluted with distilled water, then with 5% ethanol, then with 10% ethanol, then with 20% ethanol, then with 30% ethanol, then with 40% ethanol, and then with 50% ethanol. In some cases, one or more of the elution steps can be omitted. For example, elution can proceed directly from the 20% ethanol elution to the 50% elution without conducting the 30% and 40% ethanol elutions. Alternatively, elution can be carried out using a water/ethanol gradient solventsystem. Generally, the order of elution when using carbon-celite is as follows: D-chiro-inositol, myo-inositol, monosaccharides, Fagopyritol B1, galactinol, Fagopyritol A1, trehalose, Fagopyritol B2, sucrose, di-galactosyl myo-inositol, Fagopyritol A2, and Fagopyritol B3.

The composition of various fractions can be analyzed by evaporating aliquots from the fractions to dryness, derivitizing with trimethylsilylimidazole ("TMSI") in pyridine (1:1) to produce trimethylsilyl ("TMS") derivatized carbohydrates, and analyzing the TMS-derivatized carbohydrates by, for example, high resolution gas chromatography. By pooling fractions containing one particular fagopyritol and evaporated to dryness, substantially pure fagopyritol is produced. Fractions containing mixtures of fagopyritols can be rechromatographed to effect their separation.

The present invention also relates to a composition which includes two or more of Fagopyritol A1, Fagopyritol A2, Fagopyritol B1, Fagopyritol B2, Fagopyritol B3, and D-chiro-inositol. Preferably, this composition includes at least one isolated Fagopyritol A1, Fagopyritol A2, or Fagopyritol B3. Illustrative compositions are those which include isolated Fagopyritol A1 and isolated Fagopyritol A2, Fagopyritol B2 and isolated Fagopyritol B3, D-chiro-inositol and isolated Fagopyritol B3, and the like. Preferably, the composition is substantially free of one or more of galactinol, myo-inositol, digalactosyl myo-inositol, phytin, aromatic materials (e.g. polyphenols and pigments and other colored aromatic materials), cell wall particles, proteins, and acids (e.g. organic acids, nucleic acids, and amino acids) and their salts. It was observed that a mixture of fagopyritols was degraded within 6 hours in the presence of human fecal bacteria under in vitro conditions in the laboratory. Therefore, it is believed that the fagopyritols pass to the lower digestive tract where they are digested by bacteria to release free D-chiro-inositol for uptake.

The aforementioned fagopyritols and compositions are useful in treating diabetes in patients, such as mammals, including dogs, cats, rats, mice, and humans, by administering an effective amount of the above-described isolated fagopyritols, substantially pure fagopyritols, or compositions to such patients. For example, the substantially pure fagopyritols, the compositions, or one or more of the isolated fagopyritols of the present invention can be administered alone, or the isolated fagopyritols of the present invention can be administered in combination with suitable pharmaceutical carriers or diluents. The diluent or carrier ingredients should be selected so that they do not diminish the therapeutic effects of the fagopyritols or compositions of the present invention. Suitable pharmaceutical compositions include those which include a pharmaceutical carrier and, for example, an isolated Fagopyritol A1, an isolated Fagopyritol A2, or an isolated Fagopyritol B3. The pharmaceutical composition can, additionally, contain Fagopyritol B1, Fagopyritol B2, or both.

The fagopyritols and compositions herein can be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration. The preferred route for administration is oral. In cases where the fagopyritols are administered topically or parenterally, it is preferred that the fagopyritols be pre-hydrolyzed.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate. Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

For oral administration either solid or fluid unit dosage forms can be prepared. For preparing solid compositions, such as tablets, a suitable fagopyritol or composition, as disclosed above, is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed fagopyritols or compositions with an inert pharmaceutical diluent and filling the fixture into a hard gelatin capsule of appropriate size. Soft gelatin capsules are prepared by machine encapsulation of a slurry of the fagopyritol or composition with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

When the fagopyritols or compositions are administered orally, suitable daily dosages can be based on suitable doses of free D-chiro-inositol, such as those described in U.S. Pat. No. 5,124,360 to Larner et al., which is hereby incorporated by reference. It is believed that about half of the fagopyritols as extracted is D-chiro-inositol, mostly as bound D-chiro-inositol with small amounts of free D-chiro-inositol. Therefore, suitable doses of fagopyritol are about twice the suitable doses of D-chiro-inositol. Typically, for oral administration, suitable daily doses are from about 50 mg to about 200 mg of the fagopyritol or composition per kilogram of the subject's body weight.

Alternatively, the fagopyritols of the present invention can be administered orally in foodstuffs. For example, fagopyritols can be incorporated in purified form or in the form of buckwheat bran in bread, bread rolls, or other foodstuffs to form an edible product for consumption of fagopyritols. Fortification of breads, bread rolls, and other foodstuffs with extracted fagopyritols can provide a way to incorporate larger quantities of fagopyritols into a daily diet. Suitable procedures for bread preparation can be found, for example, in Brown, *The Tassajara Bread Book*, Boston: Shambhala Publications (1986), which is hereby incorporated by reference.

For parenteral administration, fluid unit dosage forms are prepared utilizing the aforementioned fagopyritols or compositions and a sterile vehicle, water being preferred. The fagopyritol or composition, depending on the vehicle and concentration used, can be either suspended or dissolved in the vehicle. In preparing solutions, the fagopyritol or composition can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the fluid unit dosage form can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the fagopyritol or composition is suspended in the vehicle instead of being dissolved, and sterilization cannot be accomplished by filtration. The fagopyritol or composition can be sterilized by exposure to ethylene oxide before suspending in the sterile vehicle. Advantageously, a surfactant or wetting agent is included in the parenteral suspension to facilitate uniform distribution of the fagopyritol or composition. Parenteral dosages can range from about 5 mg to about 200 mg of fagopyritol or composition per kilogram of the subject's body weight per day.

Preferably, the daily parenteral dosage would be considerably less than the dose per kilogram of subject body weight, considering that, in oral administration, the galactose from the fagopyritols would be consumed by microbes in the digestive tract whereas, in parenteral administration the galactose would contribute to blood sugar levels.

Alternatively, the fagopyritol or composition can be incorporated into a sustained release formulation and surgically implanted using conventional methods. Suitable sustained release matricies include those made of ethylene vinyl acetate and other bicompatible polymers.

As indicated above, it is believed that the fagopyritols are digested in the digestive tract by bacteria to release free D-chiro-inositol for uptake. It is known that D-chiro-inositol is an anti-oxidant and, more particularly, a hydroxyl radical scavenger. Accordingly, the fagopyritol and compositions of the present invention can also be used as a source of the antioxidant D-chiro-inositol, for example, by administering, preferably orally, the subject fagopyritols and compositions to a subject.

The present invention is further illustrated by the following examples.

EXAMPLES

Example 1

Materials and Methods

Plant Materials. Embryos of common buckwheat (*Fagopyrum esculentum* Moench cv. 'Mancan', Polygonaceae) were analyzed for soluble carbohydrates and cyclitols during seed development and in mature seeds. Mature seeds of common buckwheat cv. 'Manor' and 'Tartary' buckwheat (*Fagopyrum tartaricum* (L.) Gaertn.) also were analyzed. Buckwheat plants were grown in a greenhouse at 24° C. day (14 h) and 18° C. night (10 h) as described previously (Horbowicz et al., "Changes in Sterols and Fatty Acids of Buckwheat Endosperm and Embryo During Seed Development," *J. Agric. Food Chem.,* 40:745–750 (1992), which is hereby incorporated by reference). Natural sunlight was supplemented 14 h daily with approximately 740 $\mu$mol m$^{-2}$s$^{-1}$ incandescent light from 1000-watt Sylvania metal halide lamps. Embryos were removed from seed harvested at 6 to 32 DAP and at maturity. To evaluate the effect of temperature, 4-week-old plants from the greenhouse were transferred to growth chambers at 18 and 25° C. constant temperature until seed maturity. Plants received 16 h of fluorescent light daily at about 300 $\mu$mol m$^{-2}$s$^{-1}$. Plants with pin-type flowers and plants with thrum-type flowers were pollinated by hand by legitimate cross pollination, pin×thrum and thrum×pin, between plants within the same temperature regime in growth chambers or greenhouse. Fresh and dry weight, water, and water concentration are expressed as mean±SE of the mean for three replications of 6 to 10 seeds per treatment for pericarp, dehulled groat (seed), embryo, and endosperm on greenhouse-grown plants. For analysis of soluble components in axis and cotyledon tissues, three replications of 10 embryos each were divided into axis and cotyledon fractions. For analysis of endosperm and embryo fractions, three replications of three mature, dry, and dehulled (pericarp removed) seeds where separated by hand into embryo and endosperm fractions. The endosperm fraction contained seed coat but not pericarp. For comparison among cultivars and species, three replications of three dehulled groats each were analyzed.

Carbohydrate and Cyclitol Standards. Glucose, fructose, galactose, sorbitol, maltose, maltotriose, maltotetraose, myo-inositol, sucrose, raffinose, stachyose, phenyl $\alpha$-D- glucoside (internal standard), quercetin, and rutin were purchased from Sigma Chemical Co. (St. Louis, Mo.). Galactinol was a gift from T. M. Kuo (Peoria, Ill.); D-ononitol, sequoyitol, and L-(+)-bornesitol were gifts from F. A. Loewus (Pullman, Wash.); D-chiro-inositol and D-pinitol were gifts from S. J. Angyal (Kennington, New South Wales Australia); O-α-D-galactopyranosyl-(1→2)-4-O-methyl-D-chiro-inositol (galactopinitol A), O-α-D-galactopyranosyl-(1→3)-3-O-methyl-D-chiro-inositol (galactopinitol B), D-pinitol, and D-chiro-inositol were gifts from J. G. Streeter (Wooster, Ohio); verbascose, D-chiro-inositol, L-chiro-inositol, and D-pinitol were gifts from P. W ürsch (Lausanne, Switzerland); verbascose and D-chiro-inositol were gifts from P. Adams and R. G. Jensen (Tucson, Ariz.); and D-chiro-inositol and L-chiro-inositol were gifts from A. Richter (Vienna, Austria).

Extraction and Analysis of Soluble Carhohydrates. Axis and cotyledon tissues from three replicates of 7 embryos at 20 DAP or 5 to 10 embryos of developing (6 to 32 DAP) and mature, dry seeds were separated, weighed, and thoroughly homogenized in a mortar with 0.6 ml of ethanol:water (1:1 v:v) containing 100 μg of phenyl α-D -glucoside as internal standard. The homogenate and rinse were combined in a 1.5-ml microfuge tube, heated at 80° C. for 45 min to inactivate endogenous enzymes, and centrifuged in a Beckman Microfuge E at full speed for 20 min. The residue was re-extracted, and the combined supernatants were passed through a 10,000 $M_r$ cutoff filter. Aliquots of the filtrate were transferred to silylation vials and evaporated to dryness in a stream of nitrogen gas. The residues were kept overnight in a desiccator over phosphorus pentoxide to remove traces of water. The dry residues were derivatized with 200 μl a of silylation mixture (TMSI:pyridine, 1:1, v:v) in tightly capped silylation vials (Supelco, Belfonte, Calif.) at 70° C. in an aluminum block heater for 30 min and then cooled to 22° C. One μl of the soluble carbohydrates derivatized by TMSI was injected into a split-mode injector of a Hewlett Packard 5890 Series II gas chromatograph equipped with a flame ionization detector and a Hewlett Packard 3396A Integrator. Soluble carbohydrates were analyzed on a DB-1 capillary column (15 m length, 0.25 mm ID, and 0.25 μm film thickness; J&W Scientific, Folsom, Calif.) operated with a programmed initial temperature of 150° C., adjusted to 200° C. at 3° C./min, adjusted to 325° C. at 7° C./min, and held at 325° C. for 20 min. The injector port was operated at 335° C., and the detector was operated at 350° C. The carrier gas was helium at 3.0 ml/min, split 1:50. The detector gas was hydrogen at 30 ml/min and air at 300 ml/min.

Quantities of soluble carbohydrates were determined by extrapolation from standard curves, and the ratios of the area of peaks for each known saccharide or cyclitol to the area of the peak for phenyl α-D-glucoside, the internal standard, were plotted against known amounts of each component. All standards were dissolved in ethanol:water (1:1, v:v) before analysis to capture the anomeric forms as TMS derivatives. Amounts of unknown carbohydrates were estimated by calculation with nearest known standard. Quantities are expressed as mean+SE of the mean for three replications of each treatment.

Fractionation of Fagopyritols of Buckwheat Seeds. Soluble components extracted in ethanol:water (1:1, v:v) were evaporated to dryness. The residue was dissolved in 5 ml of acetonitrile:water (75:25, v:v) and chromatographed on a 9×290 mm column filled with 3-aminopropyl bonded silica gel, 9% functionalized (Aldrich Chemical Company, Inc. Milwaukee, Wis.). Components were eluted at 0.4 ml/min gravity flow with acetonitrile:water (75:25, v:v, for fractions <70; and 60:40, v:v, for fractions >70). One ml of each 5-ml fraction was evaporated to dryness and analyzed by gas chromatography as described above. A 1-ml sample of selected fractions was evaporated to dryness for enzymatic and/or acid hydrolysis.

Enzymatic Digestion. One ml of green coffee bean α-galactosidase (EC 3.2.1.22) (Boehringer Mannheim Corporation, Indianapolis, Ind.) in 3.2 M ammonium sulfate was dialyzed overnight against 1000 ml of distilled water to remove the ammonium sulfate that interferes with the silylation reaction and causes variable results. Dialyzed enzyme in 0.1 ml of water was added to carbohydrate or cyclitol in 0.1 ml of water and incubated at 37° C. After 24 h, 0.2 ml of absolute ethanol and 100 μg of internal standard were added. The mixture was heated to 90° C. for 5 min to inactivate the enzyme and centrifuged through a 10,000 $M_r$ cutoff filter. The filtrate was evaporated to dryness in a stream of nitrogen gas, silylated, and analyzed by gas chromatography as above.

Acid Hydrolysis. Dry samples of selected compounds were hydrolyzed with 2 N TFA for 3 h at 70° C. Compounds and hydrolysis products were identified by comparison to authentic standards by gas chromatography or by gas chromatographymass spectroscopy ("GC-MS") and/or proton nuclear magnetic resonance ("$^1$H-NMR").

Desiccation Tolerance. Immature seeds were removed from plants at 6 to 32 DAP, dehulled (pericarp removed), and germinated fresh or tested for desiccation tolerance (Blackman et al., "Maturation Proteins and Sugars in Desiccation Tolerance of Developing Soybean Seeds," *Plant Physiol.*, 100:225–230 (1992) ("Blackman I"), which is hereby incorporated by reference). Dehulled groats were dried rapidly at 12% relative humidity ("RH") over a saturated solution of LiCl at 25° C. After 6 d, seeds were humidified overnight at high relative humidity above water and germinated on wet paper towels at 25° C. Percent germination at 7 d and d-to-50%-germination are reported.

Immature seeds were harvested at 10 DAP, dehulled, and dried slowly during a 6 d period by transferring seeds daily to successively lower relative humidity (92, 87, 75, 51, 45, and 32% RH) maintained in sealed desiccators over saturated salt solutions of $KNO_3$, $Na_2CO_3$, NaCl, $Mg(NO_3)_2$, $K_2CO_3$, and $MgCl_2$, respectively (Blackman et al., "Maturation Proteins Associated with Desiccation Tolerance in Soybean," *Plant Physiol.*, 96:868–874 (1991) ("Blackman II"), which is hereby incorporated by reference). Dehulled groats (seeds) were tested for desiccation tolerance by transferring to 12% RH for 7 d and then testing the desiccated seeds (following humidification) for germination after 7 d on wet paper towels at 25° C. For the high-relative-humidity control treatment, immature seeds were placed in desiccators over water for 6 d (Blackman II, which is hereby incorporated by reference), before testing for desiccation tolerance. Embryos were removed after each step in the slow-drying process or after each day at high relative humidity and assayed for soluble carbohydrates and cyclitols.

Mature seeds of 'Mancan' commercial seedstock were germinated on wet paper towels for 0, 6, 12, 18, 24, 36, and 48 h and then rapidly dried at 12% RH over a saturated solution of LiCl as above. After 7 d of rehydration on wet paper towels at 25° C., seedlings with normal radicle growth were classified as desiccation tolerant. Axis or cotyledons were assayed for soluble carbohydrates and cyclitols.

Example 2

Olizosaccharides and Cyclitols in Embryos of Mature Seeds

Figure 2:
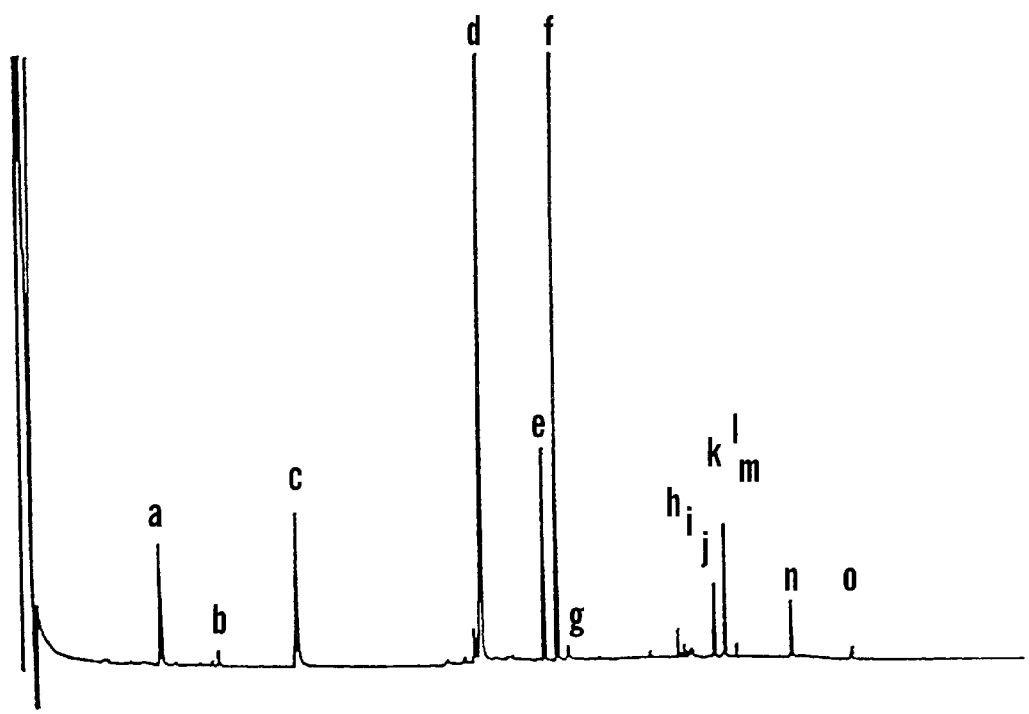
FIG. 2 is a gas chromatogram of trimethylsilylated soluble components extracted from embryo tissues of mature buckwheat seed with ethanol:water (1:1, v:v). The peaks are labeled as follows: (a) D-chiro-inositol, (b) myo-inositol, (c) phenyl α-D-glucoside (internal standard), (d) sucrose, (e) Fagopyritol A1, (f) Fagopyritol B1, (g) galactinol, (h) raffinose, (i) unknown, (j) unknown, (k) Fagopyritol A2, (l) Fagopyritol B2, (m) unknown (probably digalactosyl myo-inositol), (n) stachyose, and (o) Fagopyritol B3.

A typical gas chromatogram of soluble sugars and cyclitols extracted from embryos of mature dry buckwheat seed from commercially available registered seedstocks of 'Mancan' is shown in FIG. 2. Buckwheat embryos are believed to be unique because they accumulate galactosyl cyclitols (sugar alcohols) instead of the raffinose series oligosaccharides. A major soluble component, named Fagopyritol B1 (see FIG. 2, peak f) after the species name Fagopyrum, accumulated to 40% of the total soluble sucrose and cyclitols in buckwheat embryos. Sucrose (FIG. 2, peak d) accounted for another 42% of the total soluble sugars and cyclitols.

Fagopyritol B1 is an α-galactosyl derivative of the cyclitol D-chiro-inositol, and has the same retention time as O-α-D-galactopyranosyl-(1→2)-D-chiro-inositol, a minor component in soybean seeds (Schweizer et al., "Purification and Structure Determination of Three α-D-galactopyranosylcyclitols from Soya Beans," *Carbohydr. Res.*, 95:61–71 (1981) and Traitler et al., "Gas Chromatographic Separation of Sugars by On-Column Injection on Glass Capillary Column," *J. High Resolut. Chromatogr. Chromatogr. Commun.*, 7:558–562 (1984), which are hereby incorporated by reference). Evidence suggested that two different galactosyl chiro-inositol isomers, Fagopyritol A1 and Fagopyritol B1 (FIG. 2, peaks e and f), and two different digalactosyl chiro-inositol isomers, Fagopyritol A2 and Fagopyritol B2 (FIG. 2, peaks k and l), were present in buckwheat embryos. In addition, small quantities of Fagopyritol B3 (FIG. 2, peak o), a trigalactosyl chiro-inositol, were detected in commercial seedstocks. At least three of the five were reported not previously. Two underivatized free cyclitols, D-chiro-inositol and myo-inositol (FIG. 2, peaks a and b), were found in buckwheat. In contrast to many legume seeds that accumulate pinitol and several galactosyl derivatives of pinitol including galactopinitol A, galactopinitol B, and ciceritol (Horbowicz et al., "Seed Desiccation Tolerance and Storability: Dependence on Flatulence-Producing Oligosaccharides and Cyclitols— Review and Survey," *Seed Sci. Res.*, 4:385–405 (1994) ("Horbowicz"), which is hereby incorporated by reference), buckwheat seeds did not contain pinitol or pinitol derivatives. Buckwheat accumulated only small amounts of galacitinol (O-α-D-galactopyranosyl-(1→3)-D-myo-inositol) (FIG. 2, peak g) or digalactosyl myo-inositol (O-α-D-galactopyranosyl-(1→6)-O-α-D-galactopyranosyl-(11→3)-D-myo-inositol) (FIG. 2, peak m) (Petek I and Courtois, which are hereby incorporated by reference). Unlike maize or soybean and other legumes, such as lupine (Horbowicz, which is hereby incorporated by reference), buckwheat embryos accumulated very little raffinose (O-α-D-galactopyranosyl-(1→6)-α-D-glucopyranosyl-(1→2)-β-D-fructofuranoside) (FIG. 2, peak h) and only small quantities of stachyose (O-α-D-galactopyranosyl-(1→6)-O-α-D-galactopyranosyl-(1→6)-α-D-glucopyranosyl-(1→2)-β-D-fructofuranoside) (less than 1% of the total soluble components) (FIG. 2, peak n). No reducing sugars (glucose, fructose, galactose) were accumulated in the buckwheat embryo during seed development and maturation.

Figure 3A:
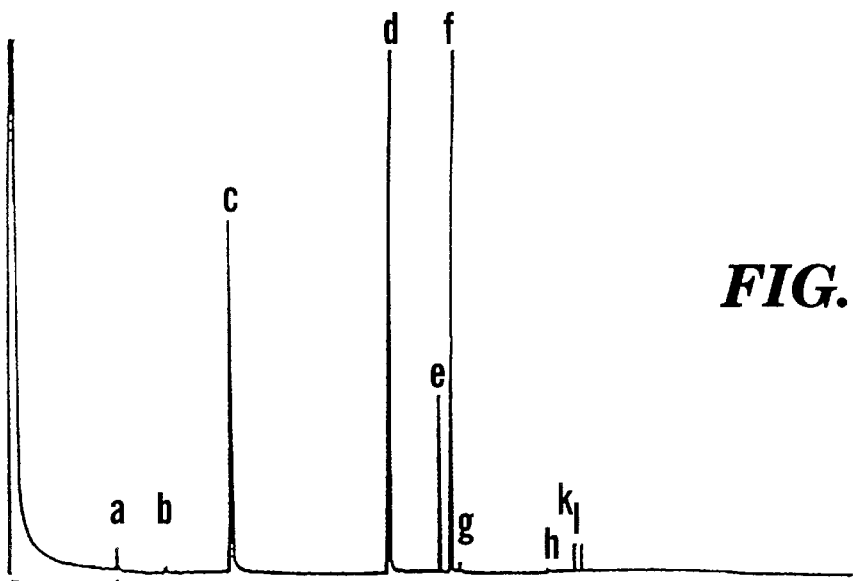
FIGS. 3A–3C are gas chromatograms of trimethylsilylated soluble components extracted from embryo tissues of 20 DAP buckwheat seed with ethanol:water (1:1, v:v).
Figure 3B:
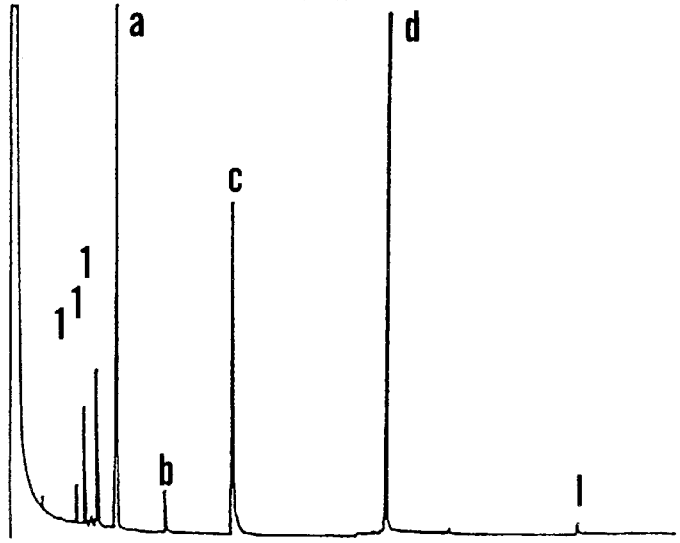
Figure 3C:
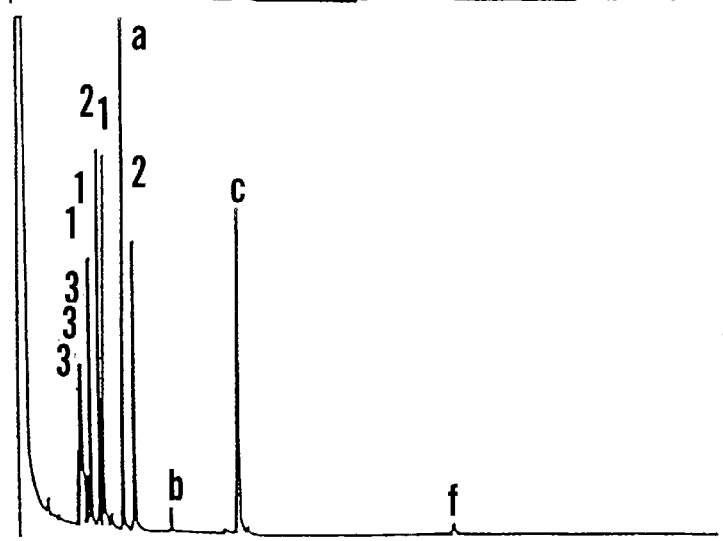

Evidence for the identity of the fagopyritol peaks is presented in FIGS. 3A–C. Before hydrolysis, the fagopyritols are readily apparent (FIG. 3A, peaks e, f, k, l). After hydrolysis with α-galactosidase, an enzyme that hydrolyses galactosyl bonds in the (alpha)-position, peaks e to l are gone (FIG. 3B) whereas D-chiro-inositol (FIG. 3B, peak a) increases greatly, and myo-inositol (peak b) increases slightly, but no other free cyclitols appear. Sucrose (FIG. 3B, peak d) does not change significantly, but anomeric forms of galactose (FIG. 3B, peaks marked "1") appear. Little sucrose and galactose result from hydrolysis of raffinose and stachyose, because these sugars are present only in trace amounts. Therefore, nearly all of the galactose was released from galactosyl cyclitols. myo-Inositol increases slightly (FIG. 3B, peak b) due to hydrolysis of galactinol (FIG. 3a, peak g) and traces of digalactosyl myo-inositol (FIG. 2, peak m). The fagopyritols were resistant to, β-galactosidase (EC 3.2.1.23) for 24 h at 37° C., and no galactose was released. This pattern confirms that peaks e, f, k, and l in FIG. 3A contained α-galactosyl linkages only. Peak 1 (Fagopyritol B2) had a retention time identical to O-α-D-galactopyranosyl-(1→6)-O-α-D-galactopyranosyl-(1→2)-D-chiro-inositol (Shiomi et al., "A New Digalactosyl Cyclitol from Seed Balls of Sugar Beet," *Agric. Biol. Chem.*, 52:1587–1588 (1988), which is hereby incorporated by reference) extracted from embryos of mature sugarbeet (*Beta vulgaris* L.) seed. After hydrolysis with a strong acid (2 N TFA), sucrose also is hydrolyzed resulting in anomeric forms of glucose (FIG. 3C, two peaks marked "2") and fructose (FIG. 3C, three peaks marked "3"). The internal standard (peak c) was added after hydrolysis. After correction for galactinol and the assumption that Fagopyritol A2 and Fagopyritol B2 are digalactosyl chiro-inositols, the products from acid hydrolysis of the tissue extract have a calculated ratio of 1.00 D-chiro-inositol to 0.93 galactose residues for Fagopyritol A1 plus Fagopyritol B1 (peaks e and j) providing evidence that both are galactosyl chiro-inositols.

Figure 4:
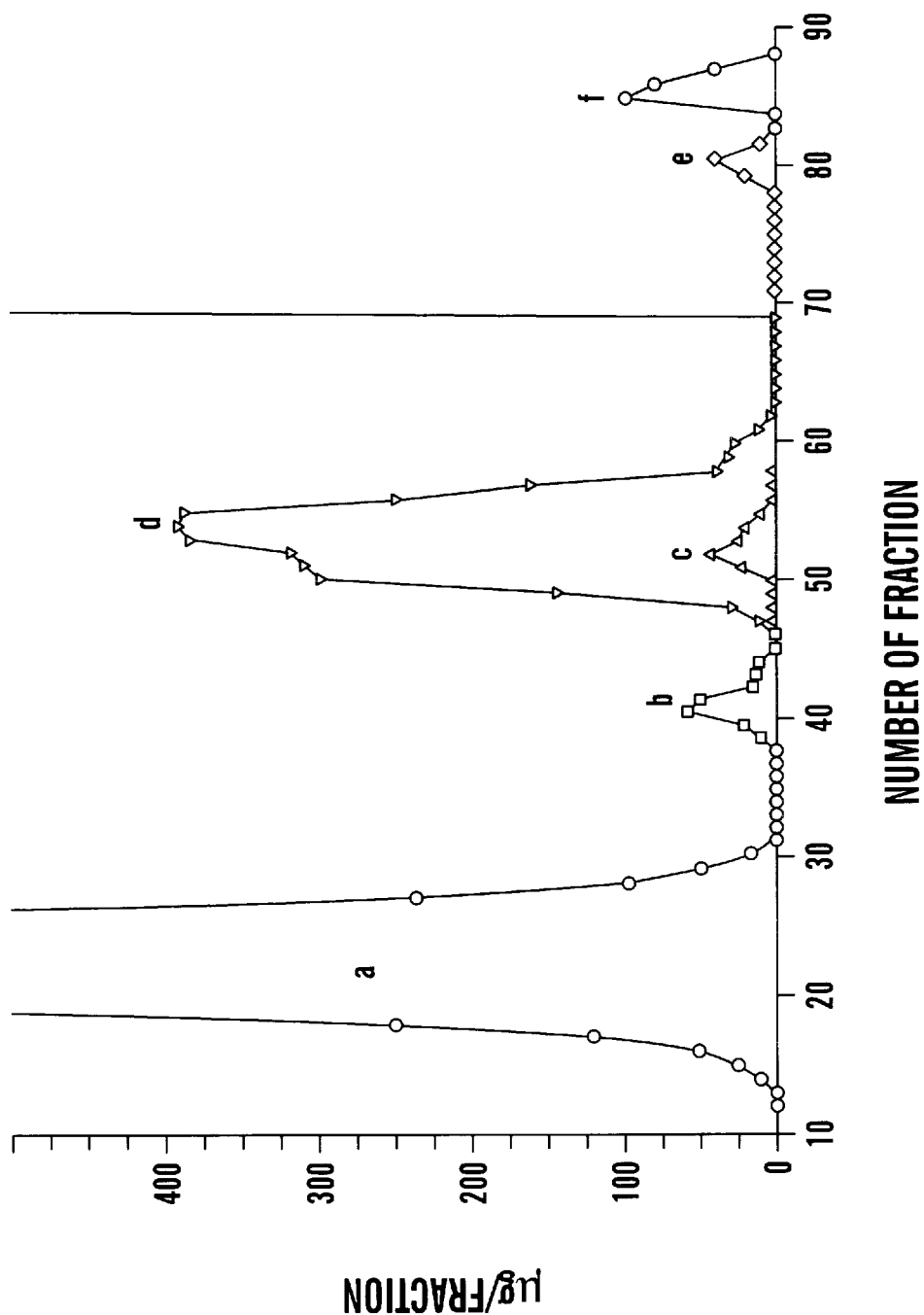
FIG. 4 is a graph showing the fractionation of fagopyritols from buckwheat seed. Mature groats were extracted with 50% ethanol, heated at 80° C. for 45 min to inactivate hydrolytic enzymes and passed through a 10,000 $M_r$ cutoff filter, and the soluble fraction was evaporated to dryness. The residue was dissolved in 5 ml of acetonitrile:water (75:25, v:v) and chromatographed on a 9×290 mm column filled with 3-aminopropyl bonded silica gel, 9% functionalized. Components were eluted at 0.4 ml/min gravity flow with acetonitrile:water (75:25, v:v) and chromatographed on a 9×290 mm column filled with 3-aminopropyl bonded silica gel, 9% functionalized. Components were eluted at 0.4 ml/min gravity flow with acetonitrile:water (75:25, v:v, for fractions 1–70; and 60:40 acetonitrile: water for fractions 71–90). One ml of each 5-ml fraction was evaporated to dryness, derivatized with trimethylsilylimidazole ("TMSI"), and analyzed by gas chromatography. A 1-ml sample of selected fractions was evaporated to dryness for enzymatic and/or acid hydrolysis. Components in each fraction are identified as follows: (a) chiro-inositol plus myo-inositol plus sucrose, (b) Fagopyritol A1, (c) unknown, (d) Fagopyritol B1, (e) Fagopyritol A2, and (f) Fagopyritol B2.
Figure 5:
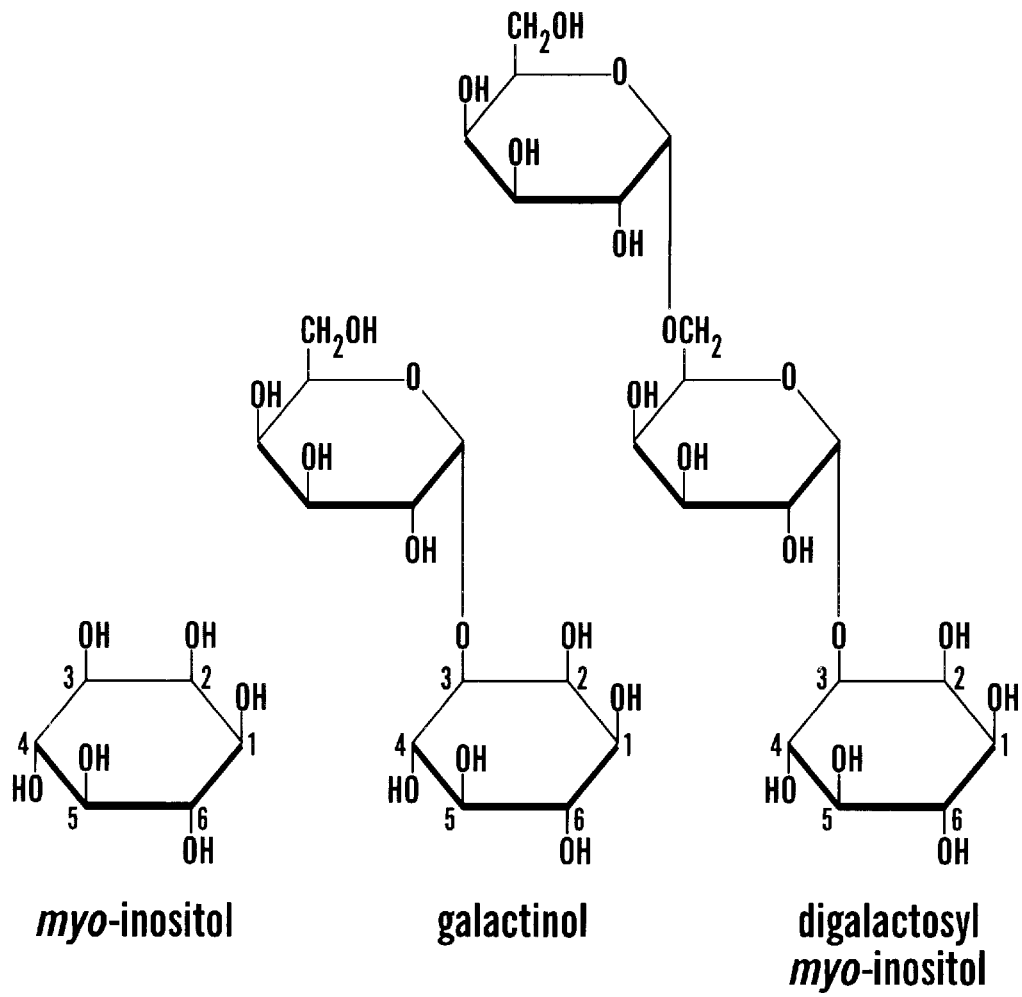
FIG. 5 shows structural formulas for the galactinol series. The enzyme synthase transfers a α-galactosyl from UDP-galactose to the 3-position of D-myo-inositol to form galactinol (O-α-D-galactopyranosyl-(1→3)-D-myo-inositol). Galactinol serves as a galactose donor to form the raffinose series oligosaccharides in many seeds. Galactinol can also serve as acceptor to form digalactosyl myo-inositol (O-α-D-galactopyranosyl-(1→6)-O-α-D-galactopyranosyl-(1→3)-D-myo-inositol) found in seeds of vetch (*Vicia sativa* L.) and other legumes (Petek et al., "Isolation of Two Galactosides of myo-Inositol from Vetch Seeds," *C.R. Acad. Sci. (Paris) Serie D: Sci. Nat.*, 263:195–197 (1966) ("Petek I"), and Petek et al., "Purification and Properties of α-Galactosidase in Germinating *Vicia sativa* seeds," *Eur. J. Biochem.*, 8:395–402 (1969) ("Petek II"), which are hereby incorporated by reference). Small quantities of higher oligomers (trigalactosyl myo-inositol and tetragalactosyl myo-inositol) may occur in legume seeds (Courtois et al., "Distribution of Monosaccharides, Oligosaccharides and Polyols," in Harborne, et al. eds., *Chemotaxonomy of the Leguminosae*, New York:Academic Press, Inc., pp. 207–229 (1971) ("Courtois"), which is hereby incorporated by reference).

For additional confirmation, fagopyritols were separated by liquid column chromatography (FIG. 4). α-Galactosidase hydrolysis products of Fagopyritol B1 (FIG. 4, peak d), after correction for galactose recovery, gave a ratio 1.00 D-chiro-inositol to 1.08 galactose confirming that Fagopyritol B1 is an α-galactosyl D-chiro-inositol. Gas chromatography analysis of the TMS-product of peak f in FIG. 4 had one peak corresponding to Fagopyritol B2. After partial hydrolysis with 2 N TFA, peaks corresponding to Fagopyritol B2, Fagopyritol B1, galactosyl galactose, D-chiro-inositol, and galactose were observed. After correction for galactose recovery, a ratio of 1.00 D-chiro-inositol to 1.93 galactose residues confirms that Fagopyritol B2 is a digalactosyl D-chiro-inositol. αc-Linkage of galactose in the fagopyritols was verified also by $^1$H-NMR. The ratio of D-chiro-inositol to galactose and the position of the peaks suggest that peaks e and f are probably different position isomers of galactosyl D-chiro-inositol, and peaks k and l are the corresponding digalactosyl D-chiro-inositols. GC-MS analysis demonstrates that Fagopyritol A1 and Fagopyritol B1 are closely related but have distinct fragmentation patterns. Structures for the galactinol series are depicted in FIG. 5.

The presence of D-chiro-inositol in Fagopyritol B1 and Fagopyritol A1 was carried our using high resolution gas chromatography and a chiral capillary column. Authenic D-chiro-inositol and L-chiro-inositol standards and the acid hydrolysis products (2 N TFA, 70° C. for 3 h) of pure Fagopyritol B1 and pure Fagopyritol A1 were derivatized with pentafluoropropionic anhydride ("PFPA"):acetonitrile (1:1, v/v). Derivatized products were co-chromatographed with standards of authentic D-chiro-inositol and L-chiro-inositol using high resolution gas chromatography with a chiral capillary column (Chirasil-Val, Alltech, Deerfield, Ill.; 25 m length, 0.25 mm inside diameter, 0.16 μm film thickness) run at 100° C. isothermally. Injection port temperature was 130° C. and flame ionization detector ("FID") temperature was 130° C. D-chiro-inositol in Fagopyritol B1 and Fagopyritol A1 co-chromatographed with authentic D-chiro-inositol (4.6 minutes retention time) but not with authentic L-chiro-inositol (4.9 minutes retention time).

Fagopyritol B1 and Fagopyritol A1 were confirmed to have only D-chiro-inositol with a retention time of 4.6 minutes.

In addition, the exact structure of the galactosyl ring, the D-chiro-inositol ring, and the α-linkage from the anomeric carbon of galactose to carbon-2 on the D-chiro-inositol ring was confirmed by NMR experiments with pure Fagopyritol B1. See Szczencinski et al., "NMR Investigation of the Structure of Fagopyritol B1 From Buckwheat Seeds," *Bulletin of the Polish Academy of Sciences Chemistry*, 40:9–13 (1998), which is hereby incorporated by reference.

Example 3
Accumulation of Sugars and Cyclitols During Seed Development and Maturation Buckwheat embryos accumulate maximum water content at 12 DAP whereas maximum fresh weight occurs at 16 DAP, and no significant increase in embryo dry matter occurs after 16 DAP (Table 1). The slight decrease in embryo dry matter noted at the latter stages of seed maturity probably reflect the difficulty encountered in physically removing all remnants of the cotyledons, which are entwined throughout the endosperm (as illustrated in Marshall et al., "Buckwheat: Description, Breeding, Production, and Utilization," *Adv. Cereal Sci. Tech.*, 5:157–210 (1982), which is hereby incorporated by reference) and adhere to the seed coat in the desiccated seed.

Table 2 shows the amounts of various carbohydrates and cyclitols present in buckwheat embryos (expressed in units of μg/embryo) at various stages during seed development and maturation. Fructose and glucose were present only in very young embryos, at 6 and 8 DAP, but not at later stages of embryo development and maturation (Table 2). D-chiro-inositol and myo-inositol were present from the earliest stages throughout embryo development and maturation (Table 2) whereas pinitol or other O-methyl cyclitols were not detected at any stage of embryo development and maturation. Sucrose increased dramatically between 8 and 10 DAP (Table 2), corresponding to the beginning of very rapid growth of the embryo (Table 1), and continued to increase at a slower rate through 16 DAP (Table 2). Fagopyritol B1 and its isomeric form, Fagopyritol A1, were first detected at 12 DAP and accumulated very rapidly between 12 and 16 DAP (Table 2). Fagopyritol A2 and Fagopyritol B2 were first detected at 16 DAP and accumulated rapidly to 20 DAP. Fagopyritol B3 accumulated at 20 DAP (Table 2) during the early phase of embryo desiccation (50 to 35% water concentration; Table 1). Total soluble sugars and cyclitols accumulated in two waves: first, 8 to 10 DAP in association with rapid embryo growth and sucrose accumulation and, second, 12 to 16 DAP in association with a rapid accumulation of Fagopyritol B1 (Table 2).

TABLE 2

| Component | 6 DAP | 8 DAP | 10 DAP | 12 DAP | 16 DAP | 20 DAP | 24 DAP | 28 DAP | 32 DAP |
|---|---|---|---|---|---|---|---|---|---|
| fructose | 1.90 ± 0.34 | 1.12 ± 0.02 | 0 | 0 | 0 | 0 | 0 | 0 | 0 |
| glucose | 2.44 ± 0.53 | 3.90 ± 0.02 | 0 | 0 | 0 | 0 | 0 | 0 | 0 |
| D-chiro-inositol | 1.07 ± 0.17 | 3.60 ± 0.58 | 3.85 ± 1.42 | 1.68 ± 0.75 | 9.64 ± 0.68 | 3.77 ± 0.34 | 3.49 ± 0.51 | 2.74 ± 0.95 | 2.26 ± 0.38 |
| myo-inositol | 0.03 ± 0.01 | 0.12 ± 0.49 | 1.06 ± 0.14 | 1.75 ± 0.13 | 3.42 ± 0.56 | 2.51 ± 0.14 | 2.71 ± 0.30 | 2.38 ± 0.12 | 3.08 ± 0.20 |
| sucrose | 6.79 ± 0.43 | 15.00 ± 0.49 | 212.2 ± 34.8 | 262.0 ± 46.9 | 295.9 ± 38.5 | 319.8 ± 19.8 | 262.0 ± 46.9 | 272.3 ± 18.1 | 300.0 ± 9.7 |
| Fagopyritol A1[a] | 0 | 0 | 0 | 0.95 ± 0.95 | 35.0 ± 4.24 | 32.88 ± 4.24 | 28.38 ± 3.07 | 21.38 ± 4.24 | 24.38 ± 4.43 |
| Fagopyritol B1[a] | 0 | 0 | 0 | 4.34 ± 2.45 | 162.2 ± 49.6 | 194.2 ± 20.3 | 163.5 ± 9.1 | 123.2 ± 22.4 | 158.2 ± 30.0 |
| galactinol | 0 | 0 | 0 | 0 | 7.84 ± 1.37 | 4.65 ± 0.51 | 4.26 ± 2.33 | 5.73 ± 0.99 | 4.18 ± 0.09 |
| raffinose | 0 | 0 | 0 | 0 | 0 | 0.34 ± 0.29 | 0.84 ± 0.09 | 0.26 ± 0.14 | 1.10 ± 0.45 |
| Fagopyritol A2[b] | 0 | 0 | 0 | 0 | 7.86 ± 3.96 | 17.36 ± 2.01 | 12.71 ± 1.37 | 8.74 ± 1.06 | 12.67 ± 2.76 |
| Fagopyritol B2[b] | 0 | 0 | 0 | 0 | 6.51 ± 3.51 | 18.56 ± 2.67 | 12.63 ± 1.71 | 10.36 ± 0.74 | 15.52 ± 3.33 |
| digalactosylmyo-inositol[b] | 0 | 0 | 0 | 0 | 0.43 ± 0.43 | 1.22 ± 0.83 | 0.69 ± 0.44 | 0.99 ± 0.53 | 1.43 ± 0.88 |
| stachyose | 0 | 0 | 0 | 0 | 0 | 0 | 0 | 0 | 0 |
| Fagopyritol B3[c] | 0 | 0 | 0 | 0 | 0 | 4.79 ± 0.56 | 3.19 ± 0.39 | 3.13 ± 0.43 | 3.43 ± 1.71 |
| Total | 12.23 | 23.74 | 217.1 ± 33.5 | 266.4 ± 48.2 | 528.8 ± 42.2 | 600.3 ± 9.5 | 495.0 ± 25.1 | 451.1 ± 11.4 | 426.2 ± 37.7 |
| suc:Fagopyritol B1[d] (ratio) | ∞ | ∞ | ∞ | 60.36 | 1.82 | 1.65 | 1.60 | 2.21 | 1.89 |
| suc:non-suc[d] (ratio) | 1.25 | 1.72 | 43.31 | 59.54 | 1.27 | 1.14 | 0.88 | 1.52 | 1.32 |

[a]Calculated on the galactinol standard.
[b]Calculated on the raffinose standard.
[c]Calculated on the stachyose standard.
[d]Ratio of sucrose to Fagopyritol B1 and ratio of sucrose to non-sucrose was calculated on mean values.

TABLE 1

| DAP | Fresh weight (mg) | Dry weight (mg) | Water (mg) | Water (g/gFW) |
|---|---|---|---|---|
| 6 | 0.43 ± 0.00 | 0.11 | 0.32 | 0.750 |
| 8 | 1.60 ± 0.29 | 0.48 | 1.12 | 0.697 |
| 10 | 7.68 ± 0.77 | 2.74 ± 0.77 | 4.94 ± 0.27 | 0.658 ± 0.042 |
| 12 | 10.36 ± 1.13 | 4.38 ± 0.63 | 5.98 ± 0.55 | 0.581 ± 0.019 |
| 16 | 11.67 ± 0.44 | 6.10 ± 0.50 | 5.57 ± 0.37 | 0.479 ± 0.033 |
| 20 | 10.18 ± 0.52 | 6.42 ± 0.28 | 3.76 ± 0.33 | 0.368 ± 0.018 |
| 24 | 7.27 ± 0.99 | 5.67 ± 0.44 | 1.60 ± 0.65 | 0.206 ± 0.056 |
| 28 | 5.83 ± 0.50 | 5.07 ± 0.67 | 0.77 ± 0.23 | 0.137 ± 0.045 |
| 32 | 5.43 ± 0.28 | 5.13 ± 0.24 | 0.30 ± 0.06 | 0.055 ± 0.008 |

Example 4
Distribution of Sugars and Cyclitols in Buckwheat Seeds

The axis was found to be 8% of the embryo fresh weight, whereas the cotyledons were 92% of the embryo fresh weight at 20 DAP (Table 3). The concentration of all components were higher in the axis than in the cotyledons (Table 3). Sucrose, cyclitols, and their derivatives accumulated to 15% of the dry weight of the axis of buckwheat embryo compared to 8% of the cotyledon dry weight (Table 3). Fagopyritol B1 concentration in axis tissues was double that in the cotyledons, and the ratio of sucrose to Fagopyritol B1 was 1.07 (w:w) in the axis compared to 1.64 in the cotyledons. The flatulence-producing oligosaccharides, raffinose and stachyose, were present in the axis tissues but only in trace amounts in the cotyledons (Table 3). Galactinol is the galactose donor to sucrose (DP-2) to form raffinose (galactosyl sucrose, a DP-3) and to raffinose to form stachyose (galactosyl sucrose, a DP-4).

TABLE 3

| Carbohydrate or cyclitol | Axis | | | Cotyledons | | |
|---|---|---|---|---|---|---|
| | (μg/embryo) | (mg/g FW) | mg/g DW) | (μg/embryo) | (mg/g FW) | (mg/g DW) |
| D-chiro-inositol | 0.76 ± 0.12 | 0.89 ± 0.14 | 1.41 ± 0.02 | 3.26 ± 1.08 | 0.32 ± 0.11 | 0.51 ± 0.17 |
| myo-inositol | 0.36 ± 0.03 | 0.42 ± 0.06 | 0.66 ± 0.09 | 3.15 ± 0.14 | 0.31 ± 0.02 | 0.49 ± 0.03 |
| sucrose | 34.77 ± 3.25 | 40.35 ± 2.50 | 63.89 ± 3.96 | 275.4 ± 73.7 | 26.59 ± 6.24 | 42.11 ± 9.88 |
| Fagopyritol A1[a] | 5.21 ± 0.12 | 6.10 ± 0.44 | 9.66 ± 0.69 | 32.26 ± 4.99 | 3.20 ± 0.60 | 5.06 ± 0.95 |
| Fagopyritol B1[a] | 32.47 ± 1.67 | 38.16 ± 3.91 | 60.43 ± 6.19 | 167.6 ± 34.2 | 16.70 ± 3.95 | 26.44 ± 6.25 |
| galactinol | 0.87 ± 0.14 | 1.02 ± 0.19 | 1.62 ± 0.30 | 5.49 ± 1.56 | 0.54 ± 0.14 | 0.85 ± 0.22 |
| raffinose | 0.14 ± 0.02 | 0.16 ± 0.02 | 0.25 ± 0.03 | 0 | 0 | 0 |
| unknown[b] | 0.55 ± 0.05 | 0.65 ± 0.10 | 1.03 ± 0.16 | 0.79 ± 0.46 | 0.14 ± 0.03 | 0.22 ± 0.05 |
| Fagopyritol A2[b] | 1.66 ± 0.01 | 1.95 ± 0.09 | 3.08 ± 0.14 | 17.40 ± 1.04 | 1.72 ± 0.16 | 2.72 ± 0.25 |
| Fagopyritol B2[b] | 2.87 ± 0.19 | 3.38 ± 0.41 | 5.35 ± 0.64 | 15.94 ± 0.79 | 1.57 ± 0.13 | 2.48 ± 0.20 |
| digalactosyl myo-inositol[b] | 0.33 ± 0.03 | 0.38 ± 0.03 | 0.60 ± 0.05 | 1.66 ± 0.75 | 0.06 ± 0.03 | 0.09 ± 0.05 |
| stachyose | 0.89 ± 0.07 | 1.05 ± 0.13 | 1.66 ± 0.20 | tr | tr | tr |
| Fagopyritol B3[c] | 1.21 ± 0.03 | 1.41 ± 0.11 | 2.23 ± 0.17 | 3.98 ± 0.51 | 0.39 ± 0.01 | 0.61 ± 0.02 |
| Total | 82.08 ± 2.24 | 95.92 ± 4.92 | 151.89 ± 7.79 | 527.4 ± 39.8 | 51.36 ± 2.75 | 81.33 ± 4.35 |
| | (ratio) | | | (ratio) | | |
| suc:Fagopyritol B1[d] | 1.07 | | | 1.64 | | |
| suc:non-suc[d] | 0.73 | | | 1.09 | | |
| | (mg/axis) | | | (mg/cots) | | |
| fresh weight | 0.86 ± 0.04 | | | 10.20 ± 0.35 | | |

[a]Calculated on the galactinol standard.
[b]Calculated on the raffinose standard. Unknown has retention time ratio of 2.44 relative to phenyl α-D-glucoside.
[c]Calculated on the stachyose standard.
[d]Ratio of sucrose to Fagopyritol B1 and ratio of sucrose to non-sucrose was calculated on mean values.

The endosperm fraction, including the aleurone layer and bran fraction of maternal seed coat-nucellus (spermoderm) tissues, was 74% of the dehulled groat, and the embryo was 26% of the dehulled groat (table 4). The embryo fraction contained 71.4% of the total soluble carbohydrates and cyclitols, and the endosperm fraction contained 28.6. The embryo contained five times as much Fagopytitol B1 (403 μg) as the endosperm fraction (76 μg) (Table 4). Most of the sugars, cyclitols, and cyclitol derivatives in the endosperm fraction were probably in the aleurone layer. Some could have been in fragments of coytledons that could not be separated completely from the endosperm fraction of mature dry groats. The concentration of soluble components in the endosperm fraction was low because starch is the major storage compartment.

TABLE 4

| Carbohydrate or cyclitol | Endosperm (mg/g dry weight) | Embryo (mg/g dry weight) |
|---|---|---|
| D-chiro-inositol | 0.25 ± 0.03 | 0.80 ± 0.16 |
| myo-inositol | 0.10 ± 0.01 | 0.27 ± 0.02 |
| sucrose | 6.99 ± 0.37 | 30.50 ± 0.84 |
| Fagopyritol A1[a] | 0.41 ± 0.04 | 2.10 ± 0.27 |
| Fagopyritol B1[a] | 2.77 ± 0.37 | 41.16 ± 2.97 |
| galactinol | 0.04 ± 0.03 | 0.29 ± 0.03 |
| raffinose | 0 | tr |
| Fagopyritol A2[b] | 0.18 ± 0.03 | 0.86 ± 0.05 |
| Fagopyritol B2[b] | 0.34 ± 0.03 | 1.50 ± 0.20 |
| digalactosyl myo-inositol[b] | 0.05 ± 0.02 | 0.13 ± 0.03 |

TABLE 4-continued

| Carbohydrate or cyclitol | Endosperm (mg/g dry weight) | Embryo (mg/g dry weight) |
|---|---|---|
| stachyose | 0 | tr |
| Fagopyritol B3[c] | tr | 0.21 ± 0.07 |
| TOTAL | 11.19 ± 0.79 (mg) | 77.82 ± 4.20 |
| dry weight | 27.3 ± 1.0 | 9.8 ± 0.8 |

[a]Calculated on the galactinol standard.
[b]Calculated on the raffinose standard.
[c]Calculated on the stachyose standard.

Example 5
Cultivar and Species Differences in Cyclitols and Soluble Carbohydrates The concentration of total soluble carbohydrates and cyclitols in mature dehulled groats was about the same in 'Mancan' and 'Manor' common buckwheat (Table 5) and in 'Tartary' buckwheat. The concentration of sucrose was the same in groats of all three genotypes. Fagopyritol B1 was highest in concentration in 'Mancan', lower in 'Manor', and only 20% as high in 'Tartary' as in 'Mancan'. 'Tartary' had two unknown compounds not found in 'Mancan' or 'Manor', whereas 'Manor' had higher concentrations of Fagopyritol A2, Fagopyritol B2, and Fagopyritol B3 (Table 5). Part of the differences may have been related to the environment of production, since the three genotypes were not grown under the same environmental conditions. However, the high concentration of unknown 1 and the low concentration of Fagopyritol B1 in groats of 'Tartary' buckwheat were probably a reflection of genetic differences. The shift to higher concentrations of the higher galactosyl oligomers in groats of 'Manor' buckwheat may have reflected environmental influences.

TABLE 5

| Carbohydrate or cyclitol | Retention time ratio (Rt) | Mancan (mg/g dry weight) | Manor (mg/g dry weight) |
| --- | --- | --- | --- |
| D-chiro-inositol | 0.51 | 0.40 ± 0.07 | 0.26 ± 0.06 |
| myo-inositol | 0.72 | 0.10 ± 0.01 | 0.14 ± 0.01 |
| sucrose | 1.71 | 13.17 ± 0.34 | 12.57 ± 1.21 |
| unknown 1[a] | 1.76 | 0 | 0 |
| unknown 2[a] | 1.81 | 0 | 0 |
| Fagopyritol A1[a] | 1.96 | 0.86 ± 0.11 | 1.10 ± 0.10 |
| Fagopyritol B1[a] | 2.01 | 12.86 ± 1.08 | 8.11 ± 0.32 |
| galactinol | 2.05 | 0.10 ± 0.01 | 0.15 ± 0.03 |
| raffinose | 2.35 | tr | tr |
| Fagopyritol A2[b] | 2.59 | 0.35 ± 0.02 | 0.82 ± 0.16 |
| Fagopyritol B2[b] | 2.63 | 0.64 ± 0.06 | 1.43 ± 0.23 |
| digaloctosyl myo-inositol[b] | 2.67 | 0.07 ± 0.02 | 0.21 ± 0.08 |
| stachyose | 2.86 | tr | tr |
| Fagopyritol B3[c] | 3.16 | 0.06 ± 0.02 | 3.38 ± 0.08 |
| TOTAL | | 28.58 ± 1.64 (mg/seed) | 25.58 ± 1.48 (mg/seed) |
| dry weight | | 37 ± 1 | 23 ± 1 |

[a]Calculated on the galactinol standard.
[b]Calculated on the raffinose standard.
[c]Calculated on the stachyose standard.

Sensitivity to the flavanols, quercetin, and rutin, was quite low by the assay methods used herein. Rutin, commonly present in buckwheat leaves, was detected only in trace amounts in groats from mature seeds of common buckwheat, either 'Mancan' or 'Manor' cultivars. In contrast, groats from mature seeds of 'Tartary' buckwheat contained about 7.14 mg of rutin per gram of dry weight, calculated with a rutin standard and, after sample hydrolysis, with quercetin and rhamnose standards. Products from acid hydrolysis of rutin were quercetin, rhamnose, and glucose. Quercetin and rhamnose were detected after acid hydrolysis (2 N TFA for 3 h at 70° C.) of extracts from 'Tartary' buckwheat groats, but neither was found in acid hydrolysis products of extracts from embryos of common buckwheat. Glucose was an acid hydrolysis product of sucrose also and, therefore, could not be used for assay of rutin in tissue extracts. Because the embryo could not be separated from the endosperm of mature dry 'Tartary' buckwheat seeds, embryo tissues could not be analyzed.

Example 6
Total Fagopyritols, Free D-chiro-inositol and Total D-chiro-inositol in Buckwheat Groats, Achenes, and Milling Fractions Among the milling fractions, the "purified bran" fraction had a high concentration of embryo fragments that adhered to the seed coats. In the absence of hulls, this fraction had the highest concentration of fagopyritols and total D-chiro-inositol among the milling fractions (Table 6). Total fagopyritols and total D-chiro-inositol concentrations in the "purified bran" were double those of the next highest milling fraction (bran #1). The concentrations of total fagopyritols and total D-chiro-inositol declined in milling fractions in the order of decreasing concentration of embryo tissues in that milling fraction (Table 6). This descending order was "purified bran">"bran #1" (with hulls)>"bran #2" (with fewer hulls) >whole groat flour>"fancy flour" (much starch)>"cracks" (with few embryo fragments). The "cracks" fraction was very difficult to pulverize and extract. The starchy endosperm of the "cracks" fraction resembled partially germinated seeds that had been dried. Upon wetting of dry seeds, α-amylase was released by cotyledons into the starchy endosperm and began to digest the starch. This sticky starch became very hard upon drying. It was postulated that some of the "cracks" come from seeds that re-wetted on the plant before harvest. The fagopyritols disappeared within 12 to 18 hours of re-wetting, and starch degradation had already started by that time. By analogy, the cracks fraction had few embryo fragments, and those fragments that were present may have reduced fagopyritols if the seed was re-wetted before harvest.

TABLE 6

| Soluble Carbohydrate | Minn-Dak Purified bran (mg/100 g) | Min-Dak bran #1 (mg/100 g) | Minn-Dak bran #2 (mg/100 g) | Minn-Dak fancy flour (mg/100 g) | Minn-Dak cracks (mg/100 g) | Minn-Dak whole groat flour (mg/100 g) |
| --- | --- | --- | --- | --- | --- | --- |
| D-chiro-inositol | 72.6 ± 3.2 | 57.8 ± 0.8 | 53.5 ± 2.8 | 14.9 ± 0.4 | 6.0 ± 0.4 | 23.3 ± 0.5 |
| myo-inositol | 35.8 ± 1.4 | 23.7 ± 1.0 | 21.5 ± 1.0 | 5.3 ± 0.8 | 2.9 ± 0.3 | 14.0 ± 0.5 |
| Sucrose | 2177.7 ± 128.7 | 1282.0 ± 61.7 | 1045.3 ± 42.5 | 344.3 ± 30.9 | 190.5 ± 7.2 | 855.6 ± 30.4 |
| Fagopyritol A1 | 208.5 ± 10.7 | 92.9 ± 4.9 | 78.2 ± 3.8 | 30.3 ± 2.9 | 10.8 ± 0.5 | 49.7 ± 3.7 |
| Fagopyritol B1 | 1335.5 ± 68.0 | 600.3 ± 37.1 | 510.7 ± 24.4 | 180.1 ± 10.3 | 68.5 ± 4.1 | 346.2 ± 24.2 |
| Galactinol | 32.2 ± 1.7 | 25.4 ± 4.0 | 19.6 ± 1.5 | 3.8 ± 0.4 | 3.1 ± 0.3 | 18.2 ± 1.3 |
| Fagopyritol A2 | 89.7 ± 3.6 | 57.2 ± 3.0 | 51.7 ± 7.6 | 14.6 ± 0.9 | 8.0 ± 0.7 | 32.0 ± 2.6 |
| Fagopyritol B2 | 120.5 ± 2.8 | 76.0 ± 1.7 | 73.6 ± 9.0 | 20.3 ± 2.6 | 14.5 ± 1.1 | 47.0 ± 4.1 |
| Digalactosyl myo-inositol | 18.9 ± 0.5 | 23.4 ± 0.8 | 20.0 ± 2.7 | 4.7 ± 0.8 | 6.1 ± 1.0 | 11.6 ± 0.9 |
| Fagopyritol B3 | 58.2 ± 0.8 | 39.5 ± 5.8 | 40.3 ± 5.4 | 10.4 ± 0.6 | 9.6 ± 1.7 | 23.2 ± 2.9 |
| Total soluble carbohydrates | 4149.5 ± 211.1 | 2278.2 ± 111.5 | 1914.4 ± 94.0 | 628.8 ± 43.9 | 319.9 ± 15.6 | 1420.7 ± 63.2 |
| Total Fagopyritols | 1812.3 ± 81.5 | 865.9 ± 51.7 | 754.5 ± 46.1 | 255.7 ± 14.3 | 111.4 ± 7.3 | 498.0 ± 34.7 |
| Total D-chiro-inositol | 929.2 ± 43.2 | 458.7 ± 23.2 | 399.8 ± 20.5 | 134.4 ± 7.2 | 55.5 ± 3.4 | 253.4 ± 15.4 |
| Free D-chiro-inositol | 72.6 ± 3.2 | 57.8 ± 0.8 | 53.5 ± 2.8 | 14.9 ± 0.4 | 6.0 ± 0.4 | 23.3 ± 0.5 |
| Water (g per 100 g of fresh wt.) | 11.6 ± 0.3 | 10.0 ± 0.2 | 9.0 ± 0.2 | 12.3 ± 0.2 | 11.4 ± 0.2 | 11.8 ± 0.3 |

Example 7
Temperature Effects on Accumulation of Sugars and Cyclitols

The sugar composition of embryos (cotyledons and axis together) is reported for embryos removed from mature seeds harvested from plants grown at 18 and 25° C. The major soluble carbohydrates in buckwheat embryos were sucrose and Fagopyritol B1, accounting for 85% of the total at 18° C. (Table 7). Since embryo dry weight was similar between the two temperatures, the endosperm accumulated an average of 15 mg more dry weight per seed at 18° C. than at 25° C. The temperature effect on the embryo soluble carbohydrates was quite interesting. Embryos of seeds grown at 18° C. had reduced sucrose, 2.5 times as much Fagopyritol B1, and three times as much stachyose as those grown at 25° C. Fagopyritol A2 and Fagopyritol B2 accumulated to higher levels at 25° C. (Table 7). When grown in the greenhouse where temperatures often exceed 25° C., Fagopyritol B3 was detectable at 20 DAP (Table 2). This pattern suggests that low temperature favors accumulation of Fagopyritol B1 while higher temperature favors accumulation of the higher galactosyl oligomers of fagopyritol. The reverse pattern occurred for stachyose. Stachyose accumulation was favored by cool temperature (Table 7) and was not detected in embryos from seeds maturing at the warmer temperatures in the greenhouse (Table 2).

TABLE 7

| Carbohydrate or cyclitol | seeds grown at 18° C. (µg/g embryo) | seeds grown at 25° C.[a] (µg/g embryo) |
|---|---|---|
| D-chiro-inositol | 13.45 ± 0.46 | 1.69 ± 0.10 |
| myo-inositol | 1.60 ± 0.32 | 1.84 ± 0.10 |
| sucrose | 211.60 ± 14.0 | 251.70 ± 6.40 |
| Fagopyritol A1[b] | 34.86 ± 5.89 | 15.65 ± 0.98 |
| Fagopyritol B1[b] | 263.50 ± 9.01 | 102.60 ± 2.95 |
| galactinol | 0 | 0.87 ± 0.44 |
| raffinose | 1.98 ± 0.49 | 2.27 ± 0.92 |
| unknown[c] | 1.45 ± 0.35 | 2.94 ± 0.66 |
| Fagopyritol A2[c] | 5.19 ± 1.68 | 10.81 ± 1.11 |
| Fagopyritol B2[c] | 6.17 ± 1.12 | 15.86 ± 2.33 |
| digaloctosyl myo-inositol | tr | tr |
| stachyose | 17.30 ± 7.45 | 5.64 ± 1.69 |
| Fagopyritol B3 | tr | tr |
| TOTAL | 557.10 ± 36.2 (mg/embryo ± SE) | 412.90 ± 9.05 (mg/embryo ± SE) |
| embryo dry weight | 5.42 ± 0.17 (mg/g dry weight) | 5.75 ± 0.52 (mg/g dry weight) |
| TOTAL soluble | 0.103 (10.3%) (ratio) | 0.072 (7.2%) (ratio) |
| sucrose/Fagopyritol B1 | 0.80 | 2.46 |
| sucrose/non-sucrose | 0.61 | 1.58 |

[a]Mature dry seeds were 47 ± 3 mg (18° C.) and 32 ± 3 mg (25° C.) before embryo excision; three replicates.
[b]Calculated on the galactinol standard.
[c]Calculated on the raffinose standard. Unknown has retention time ratio of 2.44 relative to phenyl α-D-glucoside.

Figure 6:
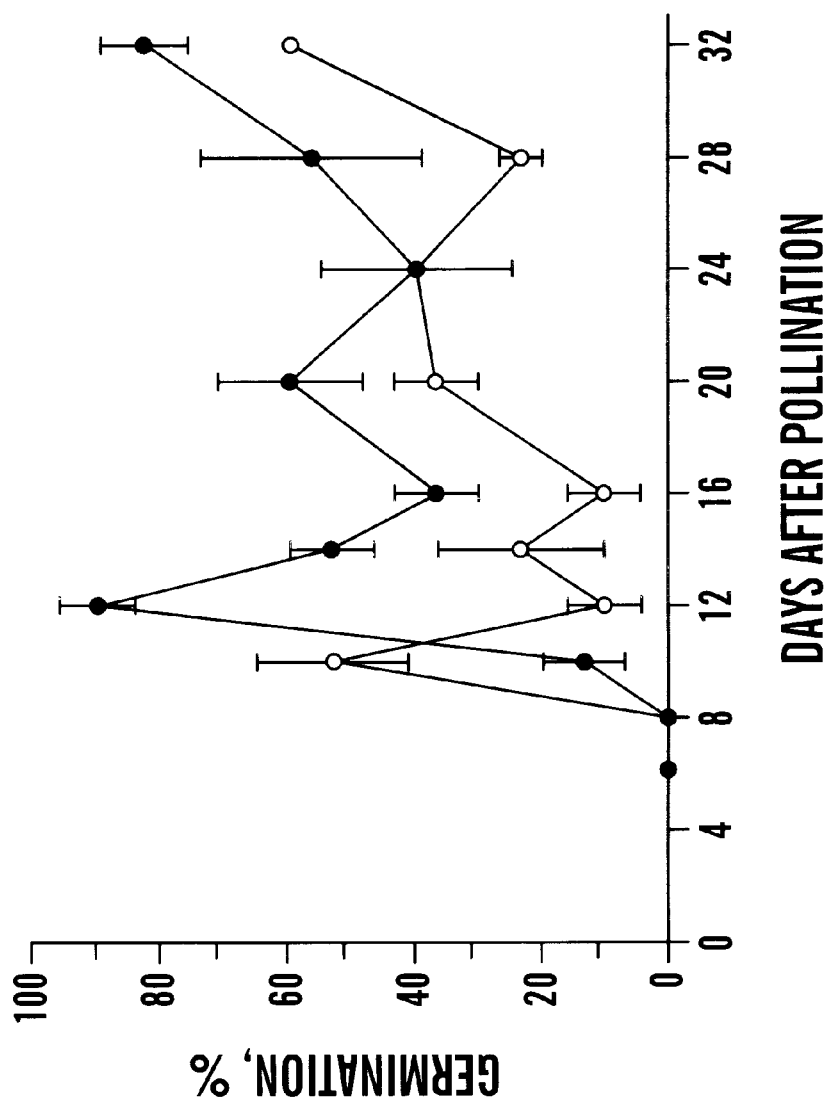
FIG. 6 is a graph showing the germination and desiccation tolerance of dehulled 'Mancan' buckwheat seeds harvested at 6 to 32 days after pollination ("DAP") and germinated fresh (○) or after rapid drying at 12% relative humidity ("RH") over a saturated solution of LiCl (●). Germination was recorded at 10 d at 25° C. on wet paper towels.

Example 8
Relationship of Fagopyritol B1 to Desiccation Tolerance During Embryo Development Developing embryos in buckwheat seeds became desiccation tolerant at 12 DAP (FIG. 6). Freshly harvested seeds exhibit a high degree of dormancy (Samimy et al., "Seed Dormancy in Common Buckwheat (*Fagopyrum esculentum* Moench.)," *Plant Varieties and Seeds*, 7:17–22 (1994), which is hereby incorporated by reference). Seeds not germinated after 16 d on wet paper towels at 25° C. were considered dormant and contained 76 to 87% as much Fagopyritol B1 (Table 8) as in planta seeds at 20 and 24 DAP (Table 2), suggesting that dormancy slows the mobilization of Fagopyritol B1. The development of desiccation tolerance at 12 DAP (FIG. 6) occurred in association with the accumulation of Fagopyritol B1 at 12 to 16 DAP (Table 2).

TABLE 8

| Carbohydrate or cyclitol | 20 DAP dormant[a] (µg/embryo) | 24 DAP dormant[a] (µg/embryo) |
|---|---|---|
| D-chiro-inositol | 8.05 ± 1.03 | 1.94 ± 0.68 |
| myo-inositol | 2.12 ± 0.30 | 1.94 ± 0.38 |
| sucrose | 224.1 ± 49.3 | 144.8 ± 24.6 |
| Fagopyritol A1[b] | 23.36 ± 0.91 | 25.47 ± 2.80 |
| Fagopyritol B1[b] | 148.1 ± 17.6 | 143.4 ± 19.7 |
| galactinol | 1.30 ± 0.65 | 1.51 ± 0.75 |
| raffinose | 0 | 0 |
| unknown, Rt = 2.49[c] | 1.19 ± 0.60 | 0.76 ± 0.76 |
| unknown, Rt = 2.51[c] | 4.05 ± 0.72 | 1.92 ± 0.96 |
| Fagopyritol A2[c] | 7.28 ± 1.36 | 8.65 ± 0.71 |
| Fagopyritol B2[c] | 7.37 ± 1.11 | 8.33 ± 1.17 |
| digalactosyl myo-inositol | tr | 0.11 ± 0.11 |
| stachyose | 0 | 0 |
| Fagopyritol B3 | 0 | 0 |
| TOTAL | 427.0 ± 43.0 | 338.8 ± 3.7 |

[a]Fresh seeds were harvested at 20 or 24 DAP. Seeds not germinating after 16 days on wet paper towels at 25° C. are considered to be dormant.
[b]Calculated on the galactinol standard.
[c]Calculated on the raffinose standard. Unknowns have retention time ratios of 2.49 and 2.51 relative to phenyl α-D-glucoside.

Figure 7A:
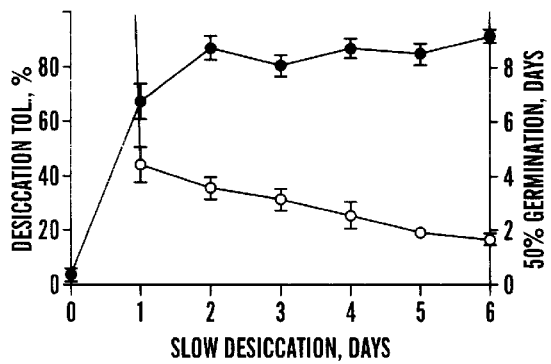
FIGS. 7A–7E are graphs showing the slow-desiccation induction tolerance in immature (10 DAP) dehulled seeds of 'Mancan' buckwheat by incubating at 93% RH during d 1, 87% RH during d 2, 75% RH during d 3, 51% RH during d 4, 45% RH during d 5, and 33% RH during d 6. Fresh seeds and seeds after incubation for 1 to 6 d at the successive lower RH environments (over saturated solutions of various salts) were rapidly dried at 12% RH and 22° C. for 1 week. After desiccation, seeds were germinated on wet paper towels at 25° C. Seeds that germinated within 7 d and had normal radicle growth were considered to be desiccation tolerant.
Figure 7B:
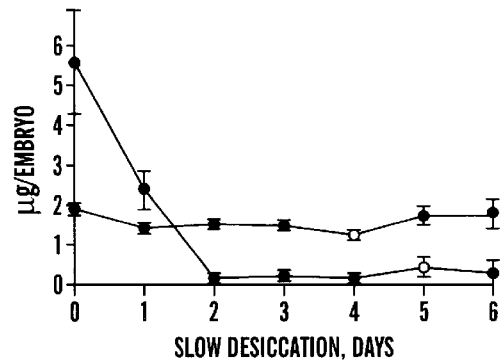
Figure 7C:
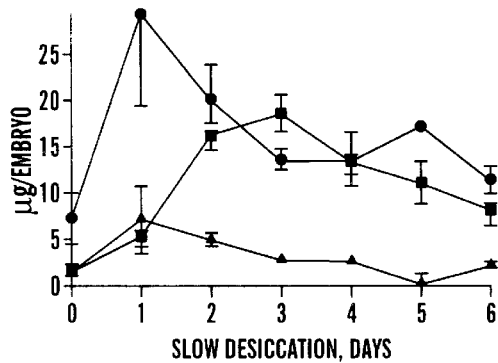
Figure 7D:
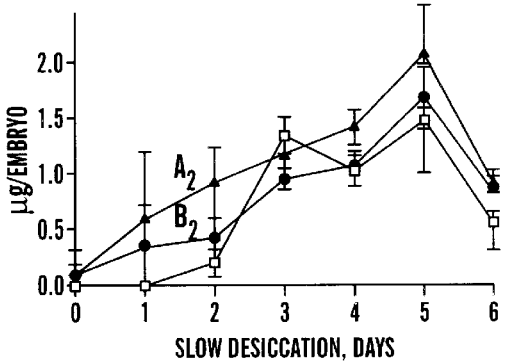
Figure 7E:
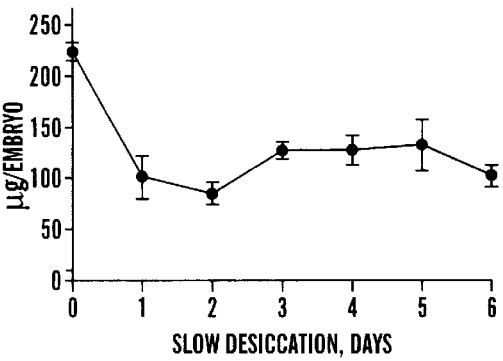

When immature buckwheat seeds were harvested at 10 DAP, desiccation tolerance was induced by slow drying under controlled relative humidities (FIG. 7A). Acquisition of desiccation tolerance during slow drying of immature seeds (precocious maturation or induced maturation) was closely associated with the accumulation of Fagopyritol B1 during the first day of slow drying (FIG. 7C). D-chiro-inositol declined rapidly during the first day of slow drying (FIG. 7B). myo-Inositol remained constant (FIG. 7B), but galactinol increased during the second day (FIG. 7C). Small amounts of Fagopyritol A2, Fagopyritol B2, and digalactosyl myo-inositol accumulated to the fifth day (FIG. 7D). Sucrose declined during the first day and then remained constant (FIG. 7E).

Figure 8A:
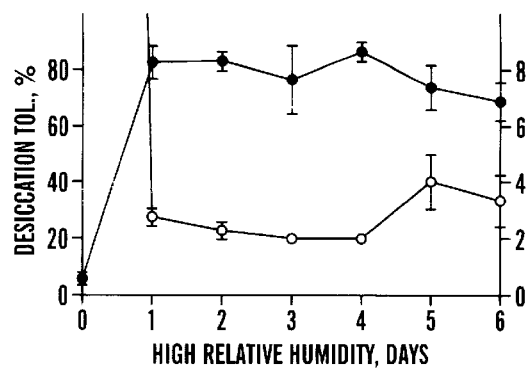
FIGS. 8A–8E are graphs showing various properties as a function of d at high relative humidity (98%) incubation of fresh 10 DAP immature dehulled 'Mancan' buckwheat seeds.
Figure 8B:
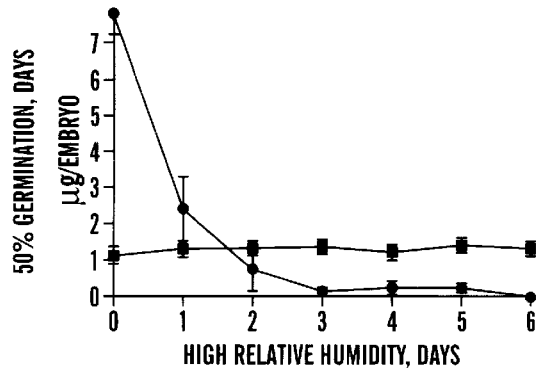
Figure 8C:
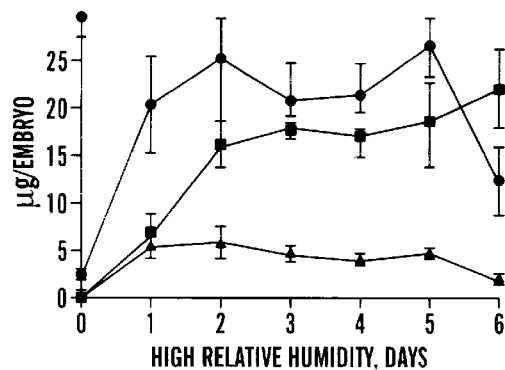
Figure 8D:
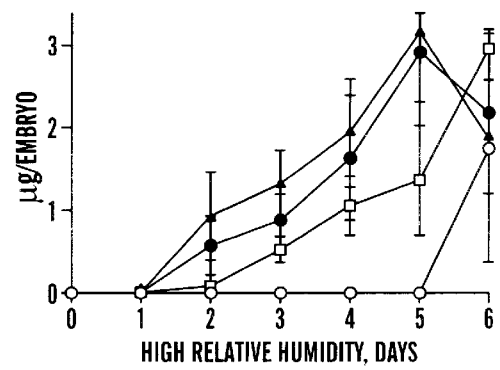
Figure 8E:
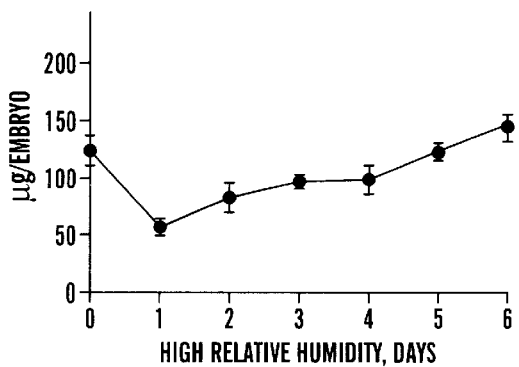

Similarly, when held at high relative humidity, immature 10-DAP dehulled buckwheat seeds became desiccation tolerant after 1 day (FIG. 8A) in association with the accumulation of Fagopyritol B1 (FIG. 8C) and the decline in D-chiro-inositol (FIG. 8B). Galactinol increased during the second day at high relative humidity (FIG. 8C). Small amounts of Fagopyritol A2 and Fagopyritol B2 accumulated 2–5 d, and digalactosyl myo-inositol accumulated 2–6 d (FIG. 8D). Fagopyritol B3 was detected only after 6 days. Sucrose increased slowly after the first day (FIG. 8E). This pattern was in contrast to axes of soybean seeds, which do not become desiccation tolerant during incubation at high relative humidity and do not accumulate stachyose during incubation at high relative humidity (Blackman I, which is hereby incorporated by reference). It appears that Fagopyritol B1 can accumulate under very mild conditions of desiccation, but accumulation of the raffinose series of oligosaccharides may require more desiccation.

Figure 9A:
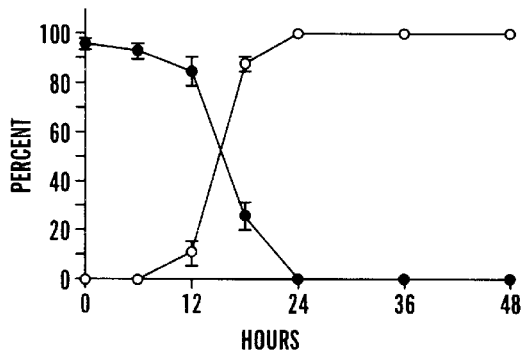
FIGS. 9A–9J are graphs showing the loss of desiccation tolerance and changes in saccharides and cyclitols during 0 to 48 h of germination of dehulled mature 'Mancan' buckwheat seeds at 25° C. on wet paper towels.
Figure 9B:
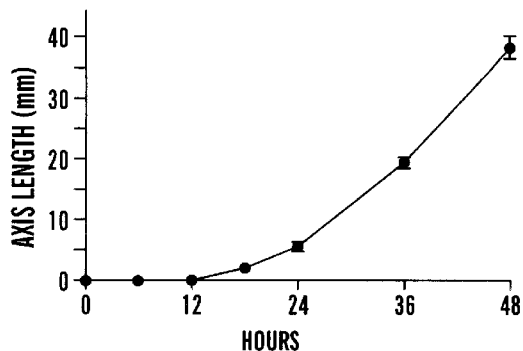
Figure 9C:
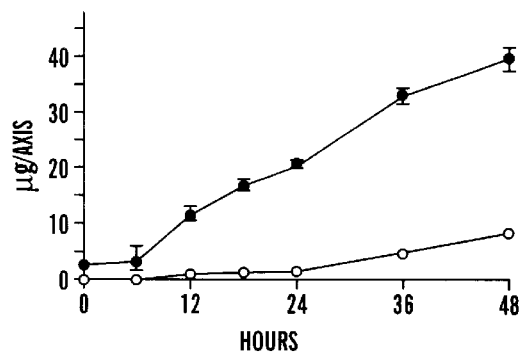
Figure 9D:
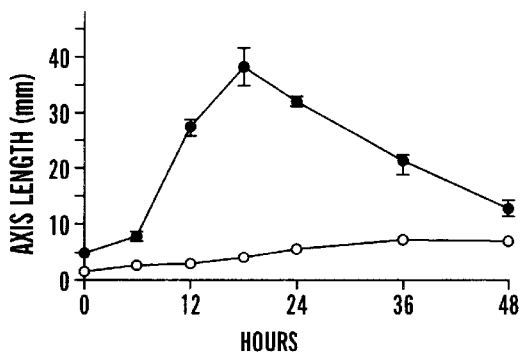
Figure 9E:
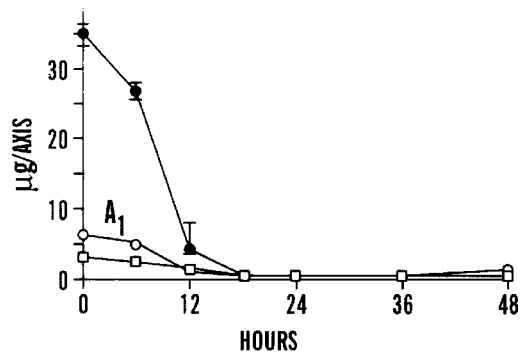
Figure 9F:
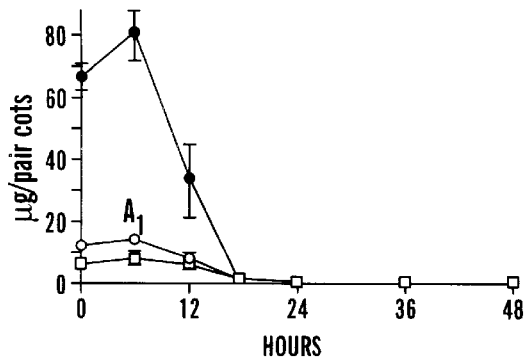
Figure 9G:
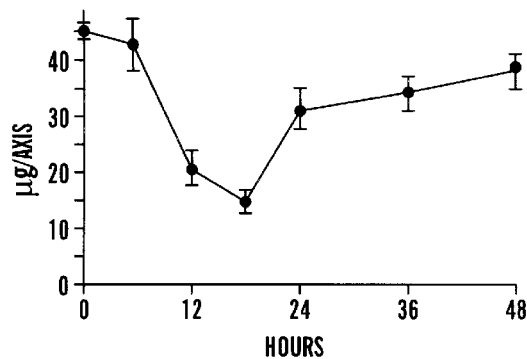
Figure 9H:
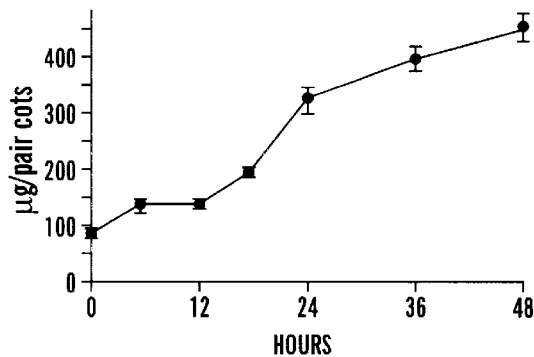
Figure 9I:
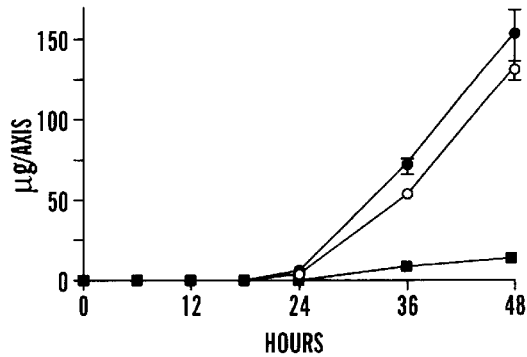

Example 9
Relationship of Fagopyritol B1 to Loss of Desiccation Tolerance During Germination The relationship of loss of Fagopyritol B1 to loss of desiccation tolerance (rapid drying at 12% relative humidity and 22° C.) was determined in axis and cotyledon tissues during germination of dehulled mature buckwheat seeds ('Mancan'). Within 6 h after the start of imbibition, Fagopyritol B1 started to disappear from axis tissues. By 12 h, only low levels remained, and by 18 h of germination, all fagopyritols completely disappeared except for trace amounts of higher oligomers (FIG. 9E). The disappearance of Fagopyritol B1 was closely associated with the onset of rapid germination and the loss of desiccation tolerance as measured by "normal" growth of the hypocotyl-radicle axis (primary root growth) upon rehydration (FIG. 9A). Sucrose levels declined and then increased after 48 h, reflecting mobilization of sugars from the cotyledons (FIG. 9G). The sucrose:Fagopyritol B1 ratio increased very rapidly after 12 h in association with the loss of desiccation tolerance and the onset of germination. In contrast to sucrose, D-chiro-inositol increases after 12 h, reflecting the hydrolysis of the fagopyritols (FIG. 9C). Galactose was not detected during mobilization of the fagopyritols but apparently was converted rapidly to other products. Fructose and glucose were present in axis tissues after 18 h (FIG. 9I) when axis tissues were growing rapidly (FIG. 9B). Fructose and glucose were the only reducing sugars in axis tissues (FIG. 9I).

Figure 9J:
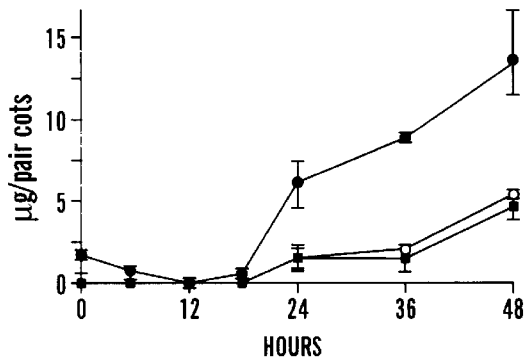

During germination maltose, maltotriose, and maltotetraose (FIG. 9J) were present in cotyledon tissues in addition to increasing levels of sucrose (FIG. 9H) reflecting the degradation of starch. D-chiro-inositol increased five fold between 6 and 18 h of germination (FIG. 9B), reflecting the degradation of fagopyritols in the cotyledons (FIG. 9F). The total amount of D-chiro-inositol (free and bound) in cotyledons declined during germination, suggesting the occurrence of transport to axis tissues or metabolism into other products. The high amount of sucrose in the cotyledons at 18 to 48 h of germination reflected the mobilization of starch in the endosperm and the absorption of hydrolysis products by the cotyledons (FIGS. 9H–J). Cotyledon tissues were imbedded in the endosperm and surrounded the starchy endosperm during germination. The lower level of Fagopyritol B1 and total soluble carbohydrates in the cotyledons at 0 h (FIG. 9F) indicated that part of the outer cotyledon, in contact with the testa (seed coat) of dry seeds, was lost during dissection of the embryo tissues from mature dry seeds.

Example 10
Materials For Fractionation Experiments

Samples of 100 dehulled seeds (about 2.5 g) were pulverized and extracted with ethanol:water (50:50). Extracts were centrifuged repeatedly, concentrated to a few ml in volume, and passed through a 10,000 $M_r$ cut-off filter. Ethanol was added to concentrated samples and placed in a freezer to facilitate precipitation of fagopyritols with the aim of concentrating Fagopyritol B3 from the crude extracts. In most cases, Fagopyritol B3 was lost or was below the level of detection in samples from the preparations.

About 97% of the sucrose was removed by invertase. Glucose, fructose, and galactose increased, and raffinose and stachyose were still present, probably because the invertase enzyme preparation was not sufficiently pure. Attempts to destroy glucose and fructose by different methods were only partially successful.

Example 11
Fractionation on P2 Gels

Several sets of extracts were pooled, concentrated, and clarified by centrifugation and ultrafiltration. The combined extracts of 1081seeds was concentrated to 3 ml. The concentrated preparation of soluble carbohydrates was loaded on a Bio-Gel P2 gel column (3 m×40 cm) and eluted with degassed water at 65° C. Early fractions were brown, and subsequent fractions were yellow in coloration. Most of the sugars and fagopyritols eluted in three 5-ml fractions and were still contaminated with brown colored material. These fractions were pooled, concentrated, and loaded onto a second Bio-Gel P2 gel column at 20° C. Fractions enriched in Fagopyritol B3 were pooled; those enriched in Fagopyritols A1 and B1 were pooled; and those enriched in Fagopyritols A1, B1, A2, and B2 and sucrose were pooled. The flow rate of the column decreased as the quantity of brown colored materials (probably polyphenolic materials) increased.

Extracts from 1300 seeds (about 35 g) were clarified by centrifugation, concentrated, and passed through a 10,000 $M_r$ cut-off filter. After concentration to 1.5 ml, the sample was ultrafiltered, and the concentrated extracts were chromatographed on P2 columns. Fractions enriched in Fagopyritol B3 and fractions enriched in other fagopyritols were combined from each of the extracts. Boiling before centrifugation resulted in swelling of starch, loss of extractable volume, and increased coloration in extracts. None of the columns resulted in efficient separation of the different fagopyritols.

Example 12
Fractionation on 3-Aminopropyl-functionalized Silica Gel Columns

A 0.9 cm×30 cm column of 3-aminopropyl-functionalized (9% functionalized) silica gel (Sigma-Aldrich) was used for fractionation of fagopyritols in subsequent experiments. Enriched fractions from the P2 gel columns were loaded on the first five amino columns.

Figure 10:
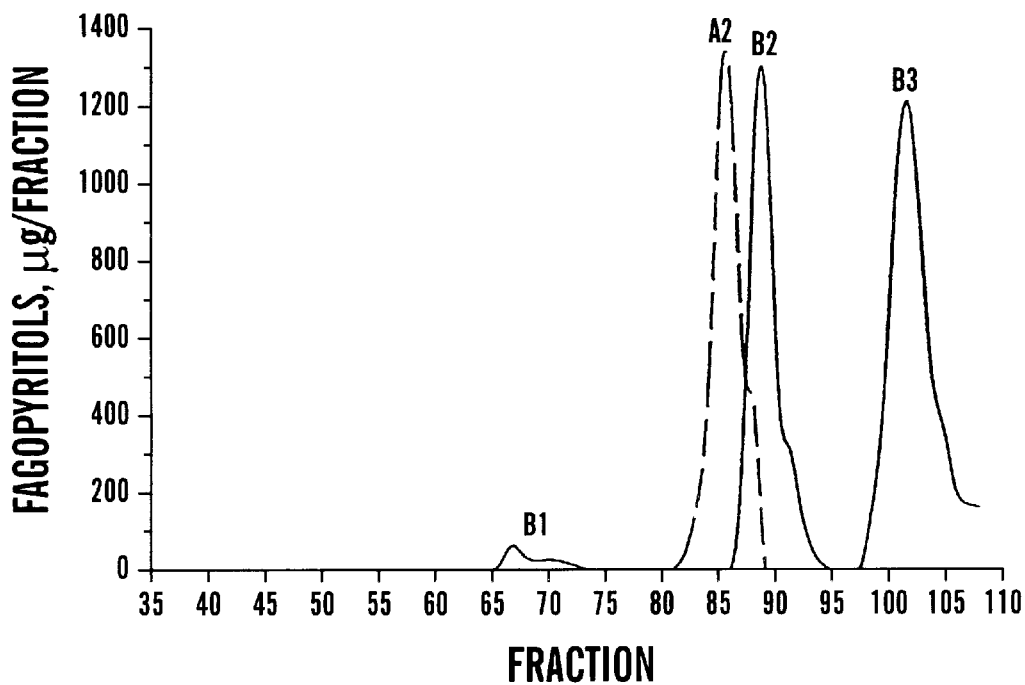
FIG. 10 is a graph of the amount of various fagopyritols present in various fractions separated on a 3-aminopropyl-functionalized silica gel column. The material loaded on the column was the enriched Fagopyritol B3 fraction collected from a P2 column.

For column 3, a sample enriched in Fagopyritol B3 after partial purification on a P2 gel column was evaporated to dryness, dissolved in 2 ml of water, and passed through a PVP column. The eluate was evaporated to dryness, dissolved in 7 ml of acetonitrile:water (70:30), and loaded onto a 0.9 cm×30 cm 3-aminopropyl-functionalized silica gel column. Stepwise elution was with 350 ml of acetonitrile:water (70:30), 150 ml of acetonitrile:water (60:40), and 50 ml of acetonitrile:water (50:50). The column was regenerated with 30 ml of acetonitrile:water (60:40) and 30 ml of acetonitrile:water (75:25). Fractions (5 ml) were collected and 0.5 ml samples from the collected fractions were evaporated to dryness and derivatized with TMSI:pyridine (1:1). The TMS-carbohydrates were analyzed by high resolution gas chromatography. Fagopyritol B3 was clearly separated from the other fagopyritols (FIG. 10). The pooled fractions containing "pure" Fagopyritol B3 were evaporated to dryness and stored for rechromatography to remove traces of contaminants. Fractions of "pure" Fagopyritol A2 or "pure" Fagopyritol B2 were pooled. Fractions of mixtures of Fagopyritols A2 and B2 were also pooled for recycling.

Figure 11:
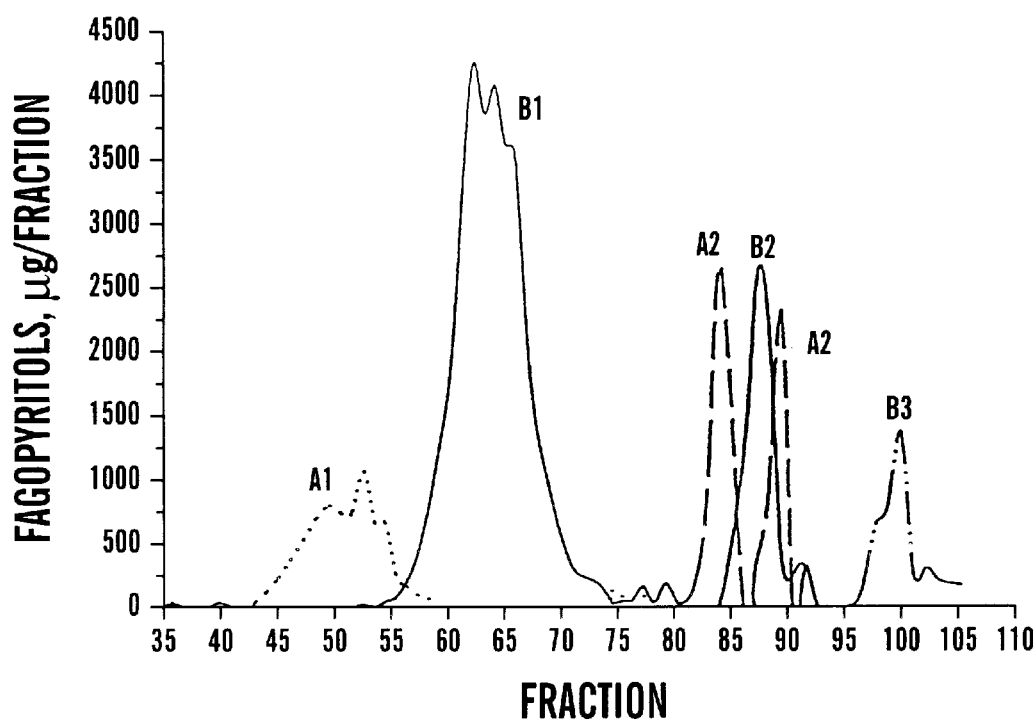
FIG. 11 is a graph of the amount of various fagopyritols present in various fractions separated on a 3-aminopropyl-functionalized silica gel column. The material loaded on the column was selected fractions from a P2 column.

For column 4, a sample containing a mixture of fagopyritols after P2 gel chromatography was further separated on aminopropyl-functionalized silica gel. (FIG. 11). Column 4 was loaded with a similar amount of Fagopyritol B3, but the other fagopyritols contributed to large total amount on the column. Fagopyritols A2 and B2 remained mixed, but several "pure" Fagopyritols A1, B1, and B3 fractions were pooled for further purification.

Example 13
Fractionation on Carbon-Celite Columns

A mixture of crude extracts was prepared from three 25 g samples of buckwheat purified bran and contained a total of 1.2 g soluble carbohydrates, of which 540 mg were fagopyritols. Purified bran was extracted with 50% ethanol, the ethanol was removed by rotary evaporation, and the extract was then passed through columns containing polyvinylpolypyrrolidone ("PVPP") and Amberlite IRN-150 ion exchange resin. The extract was then digested with yeast (2 mg yeast per g of purified bran) to remove the 97% of the sucrose. A by-product of this treatment was the disaccharide trehalose (O-α-D-glucopyranosyl-(1→1)-O-α-D-glucoside). The yeast treated extracts were filtered through a 10,000 MW cut-off filter (Amicon) and freeze dried. The combined extracts were then re-dissolved in 9 ml of distilled water and applied to the top of the carbon-Celite column. The column contained a mixture of carbon ("Darco-G60", J.T. Baker, Phillipsburg, N.J.) and Celite 545-AW (Supelco, Bellefonte, Pa.) in equal proportions by weight. The carbon-Celite mixture was slurry packed in distilled water into a 3.3 cm ID column to a height of 17 cm, and the packed column washed with 1 liter of distilled water. The column was eluted stepwise at 4° C. with 800 ml distilled water, 1000 ml 5% ethanol, 1000 ml 10% ethanol, 250 ml 20% ethanol, and 200 ml 50% ethanol. Eluate was collected in flasks which were changed by hand at hourly intervals. On average, the flasks contained a volume of 37 ml. The fagopyritol concentration contained in the fractions was analyzed by high resolution gas chromatography. The monosaccharides, glucose, and fructose (present in large quantities due to the yeast treatment) and myo-inositol and D-chiro-inositol eluted in the water fractions. Fagopyritol B1 was eluted from the column by 5% ethanol, but was contaminated with galactinol. Fagopyritols A1 and B2 were eluted by 10% ethanol, with contamination from trehalose and sucrose (the small amount not removed by the yeast), respectively. Fagopyritol A2 was contained in the 20% ethanol elution, and Fagopyritol B3 remained on the column until the 50% ethanol elution. The carbon-Celite column was more effective than the 3-aminopropyl-functionalized silica gel column in removing colored contaminants.

Example 14
Hot vs. Cold Extraction of Flour

Flour (passed 100 mesh sieve, C&N Laboratory Mill) from whole white groats (Birkett Mills) was extracted in various ratios of solvent to flour and with hot extraction or cold extraction using a Waring blender equipped with a "high shear" polytron head. The blender was on 10 sec and off 10 sec for 1 or 2 min. After hot extraction, the mixture was too thick (due to swelling of the starch) to filter or centrifuge efficiently, resulting in low volumes of extracted fagopyritols. Cold extraction (either chilled or at room temperature) resulted in highest yields. Optimum extraction was with solvent/flour ratio of 20:1 (e.g., 25 g flour in 500 ml of ethanol:water (50:50)). Relative yields of fagopyritols were about 90%, 9%, and 1% for first, second, and third extraction of the same 25 g sample. The supernatant after centrifugation or filtrate after filtration of cold extract was heated to 80° C. to inactivate alpha-galactosidase and other enzymes present in the flour that might have hydrolyzed the fagopyritols during extraction. These enzymes were inactive in ethanol:water (50:50) but may have become activated in the water phase after the ethanol is evaporated during concentration.

Example 15
Effects of Using Defatted Flour

Some samples were defatted with hexane before extraction. In these experiments, the PVP column and ion exchange column steps were carried out after ultrafiltration. Although the early steps seemed to go easier, ultrafiltration was still slow, making the whole procedure was very time consuming and laborious. To simplify the procedure and improve efficiency, further experiments were carried out with non-defatted flour.

Example 16
Extraction with Water vs. Ethanol:water (50:50)

Three replicate samples of Minn-Dak flour (200 mg each) were extracted with 2 ml of distilled water or 2 ml of ethanol:water (50:50) in centrifuge tubes. Yield of fagopyritols was the same after extraction with water or ethanol:water (50:50) (Table 9). The water extracts appeared cloudy and contained more suspended materials. This observation was probably related to the higher solubility of proteins and starch in water. The ethanol extracts contained less suspended materials and also minimized microbial and endogenous enzyme activities during extraction. Ethanol:water (50:50) was used in subsequent extractions.

TABLE 10

| Soluble carbohydrate | Birkett Mills | | Minn-Dak | |
|---|---|---|---|---|
| | mg/25 g flour | % of total | mg/25 g flour | % of total |
| D-chiro-inositol | 11.2 | 2.6 | 5.7 | 2.9 |
| myo-inositol | 8.4 | 1.9 | 3.9 | 2.0 |
| sucrose | 250.0 | 57.1 | 120.3 | 60.8 |
| Fagopyritol A1 | 22.9 | 5.2 | 11.6 | 5.9 |
| Fagopyritol B2 | 123.3 | 28.2 | 56.4 | 28.5 |
| Fagopyritol A1 | 9.2 | 2.1 | | 0.0 |
| Fagopyritol B2 | 10.2 | 2.3 | | 0.0 |
| Fagopyritol B3 | 2.6 | 0.6 | | 0.0 |
| Total | 437.8 | 100.0 | 197.9 | 100.0 |

Example 17
Comparison of Birkett Mills and Minn-Dak Flours

Sucrose and Fagopyritol B1 were the major components in both sources (Table 10). The Birkett Mills source was from whole groats and yielded about two times as much total soluble carbohydrates than the more refined flour of the Minn-Dak source. Sucrose was about 60% of the total soluble carbohydrates in both sources. Extracts from the Birkett Mills source were reddish brown in contrast to the cloudy white color the Minn-Dak extracts. Fagopyritols A2, B2, and B3 were not detected in this sample of Minn-Dak flour.

TABLE 10

| Soluble carbohydrate | Birkett Mills | | Minn-Dak | |
|---|---|---|---|---|
| | mg/25 g flour | % of total | mg/25 g flour | % of total |
| D-chiro-inositol | 11.2 | 2.6 | 5.7 | 2.9 |
| myo-inositol | 8.4 | 1.9 | 3.9 | 2.0 |
| sucrose | 250.0 | 57.1 | 120.3 | 60.8 |
| Fagopyritol A1 | 22.9 | 5.2 | 11.6 | 5.9 |
| Fagopyritol B2 | 123.3 | 28.2 | 56.4 | 28.5 |
| Fagopyritol A1 | 9.2 | 2.1 | | 0.0 |
| Fagopyritol B2 | 10.2 | 2.3 | | 0.0 |
| Fagopyritol B3 | 2.6 | 0.6 | | 0.0 |
| Total | 437.8 | 100.0 | 197.9 | 100.0 |

Example 18
Yeast Digestion of Sucrose and Fagopyritols

A 25 g sample of Minn-Dak flour was extracted with 500 ml of ethanol:water (50:50), centrifuged, heated to evaporate ethanol, and filtered. Cake yeast (8500 mg) was added to the aqueous extract and incubated at 22° C. for 0 to 48 h. About 97% of the sucrose was digested within the first 6 h, but some fagopyritols were lost, and D-chiro-inositol increased (Table 1). The large increase in myo-inositol was surprising and probably reflected a degradation of phytin in the flour. It is believed that better results could be obtained by removing the phytin with an ion exchange resin before digesting with yeast. Compared to sucrose, the fagopyritols were digested by yeast much more slowly.

TABLE 11

| Soluble | Hours Incubation | | | | | |
|---|---|---|---|---|---|---|
| Carbohydrate | 0 | 6 | 20 | 29 | 42 | 44 |
| D-chiro-inositol | 4.4 | 7.6 | 15.0 | 15.6 | 14.9 | 27.2 |
| myo-inositol | 1.2 | 15.9 | 28.9 | 22.2 | 14.7 | 24.9 |
| sucrose | 100.9 | 3.0 | 1.8 | 3.8 | 4.2 | 0.0 |
| Fagopyritol A1 | 8.8 | 8.4 | 8.9 | 7.2 | 5.0 | 9.8 |
| Fagopyritol B1 | 52.0 | 38.6 | 35.0 | 26.2 | 16.6 | 31.3 |
| Total | 188.1 | 73.5 | 89.6 | 75.0 | 55.4 | 93.2 |

In another yeast digestion experiment, the extract was passed through a PVP column, an ion exchange column, and an Amicon ultrafiltration apparatus before adding yeast. This experiment was carried out using dry granular yeast (200 mg). The results showed that sucrose was digested within the first 6 h, during which time the fagopyritols appeared to be relatively stable (Table 12). An initially unknown material increased during the first six hours and then slowly degraded. This unknown was identified as trehalose by cochromatography with authentic trehalose (after derivitization) and by gas chromatographymass spectroscopy. Retention times on the DB1 and DB5 columns and mass spectra of the unknown were identical to those of authentic trehalose. $\alpha,\alpha'$-trehalose is a dimer of glucose (O-$\alpha$-glucose-O-$\alpha$-D-glucose).

TABLE 16

| | Controls | | | Samples | | |
|---|---|---|---|---|---|---|
| | 0 hrs | 6 hrs | 12 hrs | 0 hrs | 6 hrs | 12 hrs |
| D-chiro-inositol | 99 | 102 | 58 | 47 | 0 | 0 |
| myo-inositol | 45 | 48 | 26 | 20 | 0 | 0 |
| Fagopyritol A1 | 85 | 87 | 94 | 106 | 0 | 0 |
| Fagopyritol B1 | 667 | 636 | 605 | 591 | 0 | 0 |
| Fagopyritol A2 | 56 | 54 | 59 | 54 | 0 | 0 |
| Fagopyritol B2 | 83 | 72 | 66 | 65 | 0 | 0 |
| Fagopyritol B3 | 21 | 20 | 26 | 48 | 0 | 0 |

Lower quantities of yeast were tested in a third experiment using the Birkett Mills source of flour. About 97% of the sucrose was digested by 50 mg of yeast within the first 2 h and accompanied by a doubling of glucose (Table 13). Fagopyritols appeared to be relatively stable during incubation with yeast. The lower amounts of yeast are preferred since the trehalose produced is also at a lower level. It is probably easier to remove the monosaccharide than higher molecular weight contaminants from fagopyritols.

TABLE 13

| | 50 mg yeast | | | | 100 mg yeast | | | |
|---|---|---|---|---|---|---|---|---|
| Soluble Carbohydrate | 0 h | 2 h | 4 h | 6 h | 0 h | 2 h | 4 h | 6 h |
| | | mg/25 g flour | | | | mg/25 g flour | | |
| glucose | 7.9 | 17.4 | 9.7 | 3.0 | 7.4 | 10.0 | 3.4 | 1.0 |
| D-chiro-inositol | 3.8 | 4.5 | 4.8 | 4.8 | 3.4 | 3.5 | 3.6 | 3.4 |
| myo-inositol | 1.3 | 1.4 | 1.6 | 1.6 | 1.1 | 1.1 | 1.1 | 1.3 |

TABLE 13-continued

| | 50 mg yeast | | | | 100 mg yeast | | | |
|---|---|---|---|---|---|---|---|---|
| Soluble Carbohydrate | 0 h | 2 h | 4 h | 6 h | 0 h | 2 h | 4 h | 6 h |
| | | mg/25 g flour | | | | mg/25 g flour | | |
| sucrose | 35.8 | 0.9 | | | 31.6 | | | |
| trehalose | | 2.9 | 2.8 | 2.9 | | 1.0 | 5.2 | 4.5 | 4.5 |
| Fagopyritol A1 | 7.1 | 8.1 | 8.1 | 8.2 | 6.3 | 6.4 | 6.3 | 6.0 |
| Fagopyritol B1 | 44.4 | 49.7 | 48.7 | 51.0 | 38.4 | 38.9 | 38.0 | 38.8 |
| galactinol | 0.8 | 0.9 | | 0.8 | 0.7 | 0.4 | | 0.7 |
| Fagopyritol A2 | 4.9 | 5.3 | 4.6 | 4.6 | 3.6 | 3.7 | 3.6 | 4.6 |
| Fagopyritol B2 | 6.3 | 6.5 | 5.5 | 6.2 | 4.6 | 4.6 | 4.5 | 4.6 |
| digalactosyl | 1.1 | 1.1 | | 1.1 | 0.6 | 0.5 | | |
| myo-inositol Fagopyritol B3 | 2.7 | 2.8 | | 2.3 | 2.3 | | | 2.6 |
| Total | 116.1 | 101.5 | 85.8 | 86.5 | 101.0 | 74.3 | 65.0 | 67.5 |
| % of original | 100.0 | 87.4 | 73.9 | 74.5 | 100.0 | 73.6 | 64.4 | 68.8 |

Example 19

Purification Steps

Table 14 shows the results of fagopyritol analyses at different stages (extraction, heat and centrifugation, and evaporation) during isolation from two twice-extracted 25 g samples of Birkett Mills whole groat buckwheat flour. During successive steps of purification, higher molecular weight fagopyritols appeared easier to resolve. This is believed to be partly due to increasingly pure samples and partly due to more concentrated samples in which Fagopyritol B3 is more easily resolved. The results indicated that shortening the extraction procedure may also be desirable. With cold extraction, one can use smaller volumes and still obtain good yields of extracts.

TABLE 14

| | Extraction | | Heat & centrifugation | | Evaporation |
|---|---|---|---|---|---|
| Soluble Carbohydrate | #1 | #2 | #3 | #4 | #5 |
| | | mg/25 g whole groat buckwheat flour | | | |
| D-chiro-inositol | 11.2 | 9.4 | 9.3 | 9.2 | 9.8 |
| myo-inositol | 8.4 | 7.0 | 6.7 | 6.6 | 6.3 |
| sucrose | 277.6 | 252.2 | 254.0 | 245.6 | 240.6 |
| Fagopyritol A1 | 22.9 | 20.7 | 19.2 | 19.7 | 19.6 |
| Fagopyritol B1 | 123.4 | 185.6 | 103.7 | 111.8 | 106.2 |
| Fagopyritol A2 | 9.2 | 11.0 | 10.1 | 11.7 | 11.7 |
| Fagopyritol B2 | 10.2 | 11.9 | 10.5 | 14.5 | 11.5 |
| Fagopyritol B3 | | | 7.9 | 9.2 | 6.8 |
| Total | 463.0 | 497.7 | 421.4 | 428.3 | 412.4 |

1 and #2 by 0.5 ml samples taken from two 650 ml extracts immediately after extraction.
3 and #4 by 0.5 ml samples taken from two 350 ml extracts after heating and centrifugation.
5 by 0.5 ml samples taken from 250 ml extract after evaporation and centrifugation.

The amount of fagopyritols extracted by first and second extractions are presented in Table 15. Whole groat buckwheat flour (25 g, Birkett Mills) was extracted with 320 ml of ethanol:water (50:50) during first extraction and with 200 ml of ethanol:water (50:50) during the second extraction. As Table 15shows, the first extraction removed about 90% of the soluble carbohydrates. The second extraction removed more Fagopyritol A1 but not detectable levels of the larger fagopyritols. These results indicate that shortening the extraction to a single step with lower volume would reduce extraction time but may not fully recover Fagopyritol A1.

TABLE 15

| Soluble Carbohydrate | First Extraction mg/25 g flour | % of total | Second Extraction mg/25 g flour | % of total | Total |
|---|---|---|---|---|---|
| glucose | 10.0 | 77 | 3.0 | 23 | 13.0 |
| D-chiro-inositol | 12.0 | 86 | 1.9 | 14 | 13.9 |
| myo-inositol | 5.0 | 59 | 3.5 | 41 | 8.5 |
| sucrose | 264.0 | 92 | 22.0 | 8 | 286.0 |
| Fagopyritol A1 | 2.0 | 45 | 2.4 | 55 | 4.4 |
| Fagopyritol B1 | 130.0 | 92 | 11.4 | 8 | 141.4 |
| Fagopyritol A2 | 14.0 | 100 | | 0 | 14.0 |
| Fagopyritol B2 | 14.0 | 100 | | 0 | 5.0 |
| Fagopyritol B3 | 5.0 | 100 | | 0 | 5.0 |
| Total | 456.0 | 91 | 44.2 | 9 | 500.2 |

Figure 12:
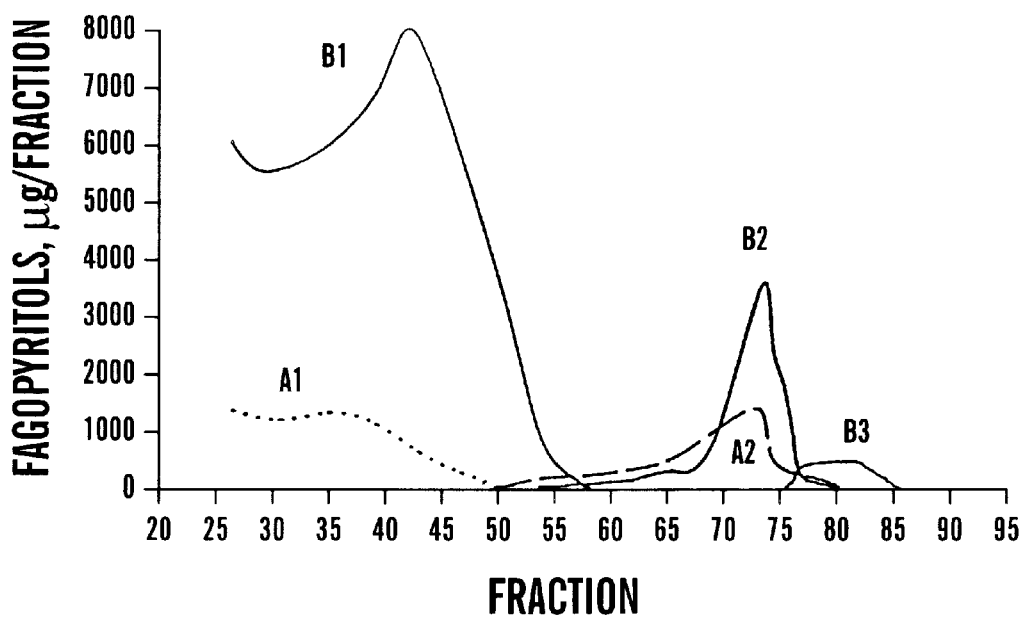
FIG. 12 is a graph of the amount of various fagopyritols present in various fractions separated on a 3-aminopropyl-functionalized silica gel column. The material loaded on the column was the extract from 50 g of whole groat flour (Birkett Mills).
Figure 13:
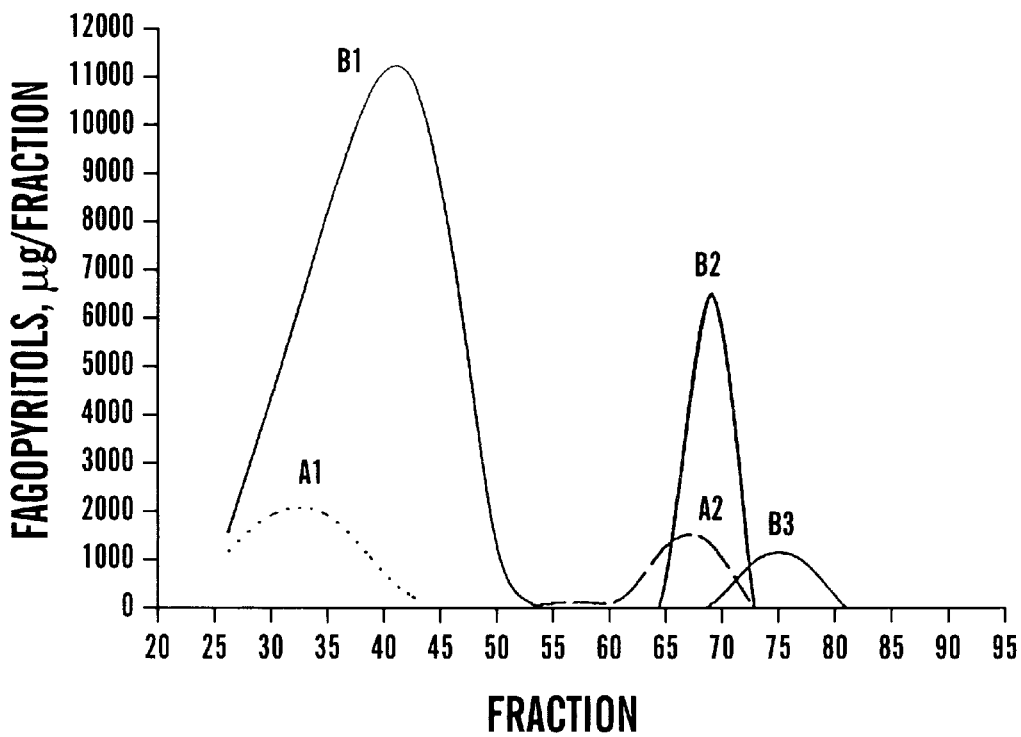
FIG. 13 is a graph of the amount of various fagopyritols present in various fractions separated on a 3-aminopropyl-functionalized silica gel column. The material loaded on the column was the extract from 50 g of whole groat flour (Birkett Mills).

The crude fagopyritol extracts could be separated into dimers, trimers, and tetramers on the 3-aminopropyl-functionalized silica gel column (FIG. 12). The column was overloaded in order to recover Fagopyritol B3. In spite of the overloading, considerable (but not total) purification was achieved. It was noted that the Fagopyritol A's and Fagopyritol B's usually overlap when the column is overloaded. However, with care, one can obtain relatively pure fractions even when the column is overloaded (FIG. 13).

Figure 14:
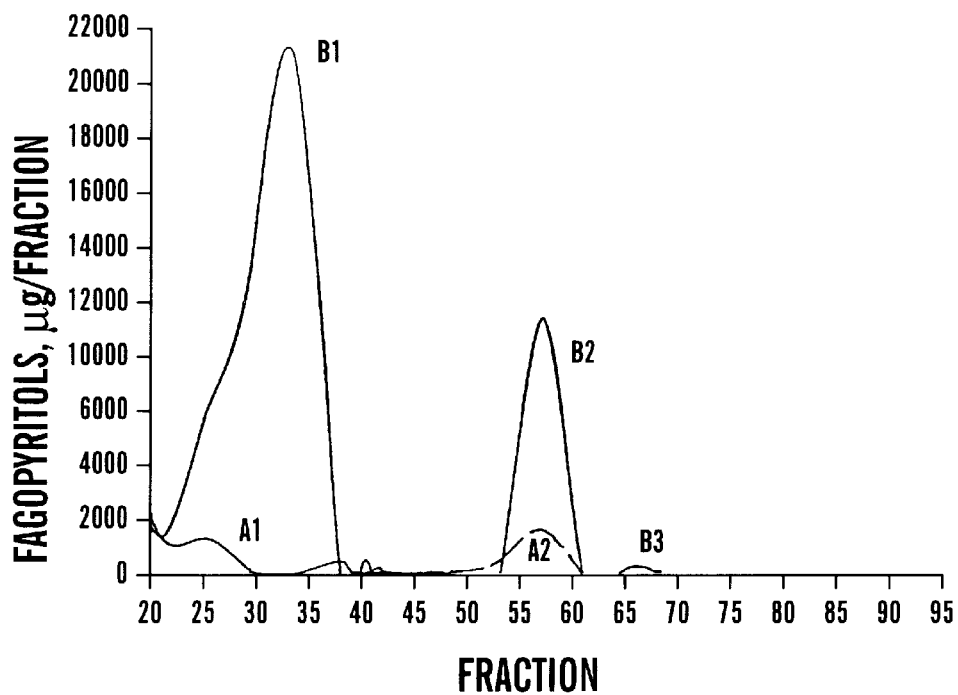
FIG. 14 is a graph of the amount of various fagopyritols present in various fractions separated on a 3-aminopropyl-functionalized silica gel column. The material loaded on the column was the extract from 50 g of whole groat flour (Birkett Mills).
Figure 15:
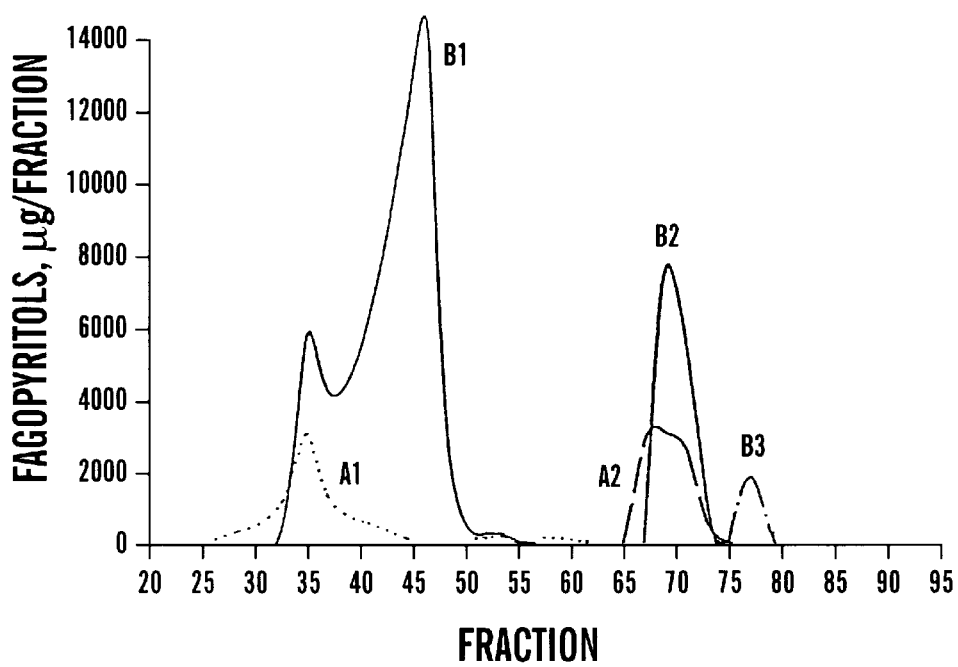
FIG. 15 is a graph of the amount of various fagopyritols present in various fractions separated on a 3-aminopropyl-functionalized silica gel column. The material loaded on the column was the extract from 50 g of light buckwheat flour (Minn-Dak).

Placing the PVP column before the ultrafiltration equipment hastened the passage of extracts through the Amicon 10,000 $M_r$ cut-off filter. As indicated by FIGS. 14 and 15, this also improved the resolution between dimer, trimer, and tetramer fagopyritols.

Example 20
In Vitro Fermentation of Fagopyritol-Enriched Buckwheat Extract by Human Fecal Microflora Fermentation tests were done with fagopyritol-enriched Birkett Mills buckwheat extract that had previously been treated with dry granular baking yeast. Yeast cells were removed by centrifugation (10 minutes at 19K rpm using a Sorvall refrigerated centrifuge) and ultrafiltration (Amicon filtration device, 10,000 MW cut-off). The fagopyritol water extract was boiled under carbon dioxide to sterilize and remove all other gases.

Anaerobic conditions were maintained during the preparation of fecal inoculum and of all samples by working under streams of carbon dioxide gas. Fermentation bottles were sealed with rubber stoppers and metal caps.

Fagopyritol substrate was prepared first. Then, 1 ml was placed in all bottles except blanks (duplicate samples plus one control and one blank done for 0, 6, 12, and 24 hours). Next, the nutritive medium was prepared. Control bottles received 1 ml of the medium in place of inoculum. The remaining medium was used to dilute fresh feces 1:12, w/v, prepared as described in Barry et al., "In Vitro Fermentation of Neutral Monosaccharides by Ruminal and Human Fecal Microflora," Acta Vet Scand, 86 (supplement):93–95 (1989) and Guillon et al., "Characterization of Residual Fibers from Fermentation of Pea and Apple Fibres by Human Fecal Bacteria," J Sci Food Agric, 68:521–529 (1995), which are hereby incorporated by reference. All samples and blanks were inoculated with 1 ml of fecal inoculum by syringe through the rubber stoppers.

A 40° C. water bath was used for the fermentation which was stopped at the specified times by opening bottles to air and immediately freezing.

The samples were prepared for GC analysis after thawing by centrifuging (microfuge, 8000 rpm) once and then again in 10,000 MW cut-off microfuge tubes. The salts present in those samples containing nutritive medium were removed by passing each sample through Amberlite mixed-bed resin, because salts interfere with TMS-derivitization.) Two control samples of the original extract were also passed through the resin to insure that fagopyritols were not removed by the treatment.

A small volume of each (750 μL) was dried with 100 μg of internal standard (phenyl α-D-glucopyranoside) in silyation vials under a stream of nitrogen gas; vials were then placed in a desiccator over $P_2O_5$ overnight.

Trimethylsilyl derivitives were prepared by adding 100 μL of 1:1 pyridine:TMS solution and heating at 70° C. for 30 minutes.

Finally, derivitized samples were analyzed on the GC (HP 5890 Series II; DB-1 column; 0.25 mm i.d., 15 m length, 0.25 μm film thickness).

Fecal bacteria removed all fagopyritol from the samples. Inositol compounds and trehalose were also metabolized by the bacteria. Two peaks (with retention times at about 3.1 and 3.4) repeated on all sample and control chromatograms indicating a by-product of the yeast treatment present in the buckwheat extract that was not metabolized by fecal bacteria; these same peaks showed in the analysis of the original extract.

The internal standard showed in all analyses indicating successful derivitization. Table 16 shows the concentrations (reported in mg/750 μL) of inositols and fagopyritols in the controls and samples.

TABLE 16

| | Controls | | | Samples | | |
|---|---|---|---|---|---|---|
| | 0 hrs | 6 hrs | 12 hrs | 0 hrs | 6 hrs | 12 hrs |
| D-chiro-inositol | 99 | 102 | 58 | 47 | 0 | 0 |
| myo-inositol | 45 | 48 | 26 | 20 | 0 | 0 |
| Fagopyritol A1 | 85 | 87 | 94 | 106 | 0 | 0 |
| Fagopyritol B1 | 667 | 636 | 605 | 591 | 0 | 0 |
| Fagopyritol A2 | 56 | 54 | 59 | 54 | 0 | 0 |
| Fagopyritol B2 | 83 | 72 | 66 | 65 | 0 | 0 |
| Fagopyritol B3 | 21 | 20 | 26 | 48 | 0 | 0 |

Example 21
Procedure for Pilot Plant Production of Fagopyritols

Milling. Buckwheat bran samples were ground using an Alpine grinder (Augsberg, Germany) with the settings on slow speed and fast feed. Ten samples of 50 pounds (22.6 kg) of bran were ground, each sample taking approximately 1.5 hours to complete, resulting in an alteration in particle size.

Extraction. Ground bran samples were placed in a 100-gallon steam-jacketed vat with a built-in air-pressure driven stirrer (Lee Metal Products, Philipsburg, Pa.). The bran samples were extracted with 66 gallons of 50% ethanol (35 gallons 95% ethanol and 31 gallons distilled water) and stirred at maximum speed for 1 hour at room temperature. The mixture was allowed to settle for 1 hour, and, once settled, the supernatant was siphoned off through a plastic hose into two 30-gallon stainless steel drums on wheels.

For runs 1 and 2 the solids remaining were then rinsed by adding a further 15 gallons 50% ethanol (8 gallons 95% ethanol and 7 gallons distilled water). This was allowed to settle, and the supernatant siphoned off. For Runs 3 to 10 the rinsing step was omitted since the technique for removing the supernatant from the first extraction was improved. This involved first filtering the clear supernatant through a diatomaceous earth plate filter ("DEPF") and then filtering as much of the sludge at the bottom of the vat as possible before the plate filter clogged.

Evaporation. The combined supernatant in Run 1 was evaporated at 60° C., with a 20 psi vacuum, in a 20-gallon capacity drum-vacuum steam-kettle (Goren, Chicago, Ill.). However, a substantial proportion of the extract was lost due to frothing up through the vacuum exhaust pipe.

In Run 2, the ethanol was evaporated by heating in a 100-gallon steam-jacketed vat. This method was effective, though time consuming (taking one full day), and resulted in ethanol fumes being released in the pilot plant.

A trial was performed with 7 gallons of the extract from Run 3 using the 20-gallon capacity drum vacuum steam kettle for evaporation, but with the exhaust hose fitted with a piece of plexiglass so that any loss of the extract could be visualized and therefore reduced by adjustment of temperature. The process was slow, as the temperature had to be lowered to 50° C. to prevent excessive frothing of the sample, and so the extract was evaporated only to 17% ethanol.

The rest of Run 3, and Runs 4, 5 and 6, were each concentrated using a Unipektin concentrator (Unipektin AG, Zurich, Switzerland). This vacuum-assisted process allowed the temperature to be maintained at 3540° C. and operated by increasing the surface area of the extract by running it through a series of long, thin pipes. Although the Unipektin was reasonably fast to use, maintaining a low temperature did not reduce the formation of the muddy-brown color, and even passing each extract through the concentrator 4 times only reduced the ethanol concentration to 5.5%. The ethanol content of the extracts was reduced to 1 to 2% by boiling in a steam jacketed 25-gallon vat (Lee Metal Products, Philipsburg, Pa.).

For the evaporation of Runs 7 to 10, the 100-gallon steam-jacketed vat was used, as described for Run 2, with ethanol vapors discharged into the pilot plant. Ethanol concentration was measured using a model 360 ebulliometer (Dujardin-Sallerson, Paris, France).

Storage of Extracts. The extracts containing fagopyritols in ethanol (before evaporation) were stored at +2° C., and the aqueous extracts (after the evaporation step) were stored at −20° C. Extracts were stored in plastic 4 or 5-gallon containers with lids.

Diatomaceous Earth Plate Filter. The diatomaceous earth plate filter ("DEPF") (T. Shriver Co., Harrison, N.J.) consists of 6 metal plates (7 inches×7 inches) with a plastic holder and piece of filter paper (Filtration Unlimited, Akron, N.Y.) on either side, all squeezed tightly together. The DEPF was prepared for use by feeding through 120 g (20 g per plate) of pre-coat mixed in water; when the water passing through the DEPF was clear, the pre-coat was in place. Body feed was stirred into the fagopyritol extract. The sample with body feed was then passed through the DEPF, with continuous stirring to keep the body feed in suspension. The diatomaceous earth powders used as pre-coat or body feed were Celite 503, Celite 535, Celite 577, and Hi-flo Super Cel ("HFSC") (Celite Corp., Lompoc, Calif.). Unless stated otherwise, the combination used was Celite 577 as pre-coat (20 g per plate) and HFSC as body feed (0.25% weight of dry powder to weight of extract).

PVPP Treatment. The polyvinylpolypyrrolidone (PVPP) used in the pilot plant extractions was Polyclar-VT (ISP Technologies, Wayne, N.J.). Where PVPP treatment was performed after the extract had been concentrated by evaporation, 0.75 kg PVPP (unless stated otherwise) was added to the extract in a 25-gallon steam-jacketed vat and stirred for 30 minutes with an air pressure-driven stirrer (Gast, Benton Harbor, Mich.). This removed some coloration but was not as effective as it had been on a laboratory bench-scale where the PVPP was loaded into a column and the extract passed through it. Increasing the treatment time to 3 hours (Run 2), as used in the wine industry, did not noticeably improve the resulting color of the extract.

For runs 7 to 10, 1.5 kg PVPP was added to the ethanolic extract of fagopyritols in the 100-gallon vat prior to evaporation. The mixture was stirred for 30 minutes and allowed to settle for a further 30 minutes, and the supernatant removed. After evaporation, the extract became a deep yellow color (soluble proanthocyanidins) rather than muddy brown (oxidized and condensed phenolics). The 0.75 kg PVPP treatment described above was also used after evaporation to further clean the extracts. Runs 7 to 10 were consequently much cleaner than the other extracts with regard to colored contaminants.

Initially, the PVPP was allowed to settle, the supernatant removed for DEPF, and the PVPP and associated liquid at the base discarded. Subsequently, it was found that the whole extract, including PVPP, could be fed into the DEPF, the PVPP being retained by the DEPF without clogging.

Bentonite Treatment. Bentonite is used in the wine industry to clear haze caused by unstable proteins in wine reacting with proanthocyanidins. The bentonite (Presque Isle Wine Cellars, North East, Pa.) was prepared by mixing (3 g per gallon of sample unless stated otherwise) with a small amount of distilled water to form a thick slurry. A blender was used to dissolve lumps. After 2 to 3 hours, a small amount of extract was mixed with the bentonite slurry, and then this was added to the rest of the extract and stirred for a few minutes. The treatment was allowed to run for approximately 24 hours in cold storage to allow flocculation to occur and proteins to precipitate. The supernatant was carefully poured off. In contrast to PVPP, the use of DEPF for removing the bentonite was not suitable, because the DEPF clogged easily.

Ion Exchange Treatment. Syburn resin (Aftech, Rochester, N.Y.) was added (1.8 kg) and stirred for 30 minutes. The resin was removed from the sample by passing through a 100-mesh sieve.

Yeast Treatment. Treatment of the extract with yeast to remove sucrose was performed for Run 2. The extract was warmed to 32° C., and 40 g of dry granular baking yeast was added and allowed to ferment for 1 hour with occasional stirring. The yeast was killed by heating to 77° C. for 15 minutes. This practice was discontinued because, although the yeast was efficient at removing the sucrose, it produced trehalose, which was difficult to separate from fagopyritol A1 during subsequent purification of fagopyritols.

Ultrafiltration. Two 10,000 MW cut-off hollow fiber filter cartridges were fitted to an ultrafiltration unit ("UF") (Romicon, Wilmington, Mass.).

Run 1 was passed through the UF early in the extraction process, quickly filtering the large volume of ethanolic extract. It was clear from this run that a large volume of liquid should be used with the UF as there was a void volume of about 5 gallons. Also, the UF should be used after most of the ethanol has been removed from the extract as the filter membranes curled slightly in the presence of 50% ethanol, though were still re-usable. Both filtration and cleaning the filters after use was found to be time and labor-intensive, so, to reduce labor costs, the other extracts were combined for their final UF treatment, rather than running each through individually.

Accordingly, extracts from Runs 2 to 10 were combined for ultrafiltration. The temperature was maintained at 27° C. throughout the 1.5 hours it took to filter the 65 gallons of total extract. Particles smaller than 10,000 daltons passed through the filter, whilst larger particles passed straight up through the cartridge and re-circulated. About 5 gallons of waste was accumulated which contained the large particulates. The filtered extract, which was collected in the 100-gallon vat, was clear and light yellow in color. The color probably reflects the presence of soluble, small molecular weight proanthocyanidins that could not be filtered by ultrafiltration and had escaped being adsorbed to PVPP, bentonite, or ion exchange resin, especially from Runs 2 to 6.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated Fagopyritol A2 having the formula:

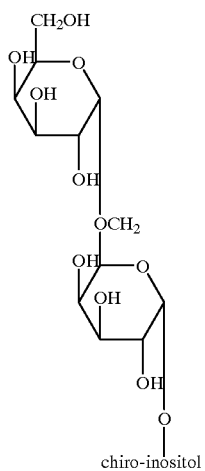

chiro-inositol

2. An isolated fagopyritol according to claim 1, wherein said fagopyritol is substantially free of one or more of galactinol, myo-inositol, digalactosyl myo-inositol, phytin, aromatic materials, cell wall particles, proteins, organic acids, amino acids, nucleic acids, and salts thereof.

3. A substantially pure Fagopyritol A2.

4. A substantially pure Fagopyritol A2 according to claim 3, wherein said Fagopyritol A2 is from about 95% to about 99% pure.

5. A composition comprised of two or more of Fagopyritol A2, Fagopyritol B1, Fagopyritol B2, and D-chiro-inositol, wherein said composition comprises the isolated fazopyritol according to claim 1.

6. A composition according to claim 5, wherein the composition is substantially free of one or more of galactinol, myo-inositol, digalactosyl myo-inositol, phytin, aromatic materials, cell wall particles, proteins, and organic acids, amino acids, nucleic acids, and salts thereof.

7. A pharmaceutical composition for use in treating type II diabetes comprising:
a pharmaceutical carrier and
an isolated fagopyritol according to claim 1.

8. A pharmaceutical composition according to claim 7, wherein said pharmaceutical composition further comprises a fagopyritol selected from the group consisting of Fagopyritol B1, Fagopyritol B2, and combinations thereof.

9. A pharmaceutical composition according to claim 7, wherein said pharmaceutical composition consists essentially of said pharmaceutical carrier and said isolated fagopyritol according to claim 1.

10. A method of treating type II diabetes in a patient comprising:
administering to the patient an isolated fagopyritol according to claim 1 in an effective amount.

11. A method of treating type II diabetes in a patient comprising:
administering to the patient a composition according to claim 5 in an effective amount.

12. A method of treating type II diabetes in a patient comprising:
administering to the patient a substantially pure Fagopyritol A2 according to claim 3 in an effective amount.

13. A method of treating type II diabetes in a patient comprising:
administering to the patient a pharmaceutical composition according to claim 7 in an effective amount.

14. A method for preparing Fagopyritol A2, Fagopyritol B1, Fagopyritol B2, or a mixture thereof comprising:
contacting buckwheat with a solvent under conditions effective to produce a crude extract comprising non-fagopyritol materials and one or more fagopyritols selected from the group consisting of Fagopyritol A2, Fagopyritol B1, and Fagopyritol B2; and
separating the non-fagopyritol materials from the one or more fagopyritols.

15. A method according to claim 14, wherein the buckwheat comprises buckwheat seed embryos.

16. A method according to claim 14, wherein the buckwheat is buckwheat flour.

17. A method according to claim 14, wherein the non-fagopyritol materials comprise one or more of cell wall particles, large proteins, charged materials, and aromatic materials.

18. A method according to claim 14, wherein said separating comprises:
evaporating the solvent under conditions effective to condense the crude extract.

19. A method according to claim 14, wherein said separating comprises:
passing the crude extract through a molecular weight cut off filter under conditions effective to remove cell wall particles and large proteins from the crude extract.

20. A method according to claim 14, wherein said separating comprises:
passing the crude extract through an ion exchange material under conditions effective to remove charged materials from the crude extract.

21. A method according to claim 14, wherein said separating comprises:

passing the crude extract through a polyvinylprrolidone column or an activated charcoal column under conditions effective to remove aromatic materials from the crude extract.

22. A method according to claim 14 wherein the one or more fagopyritols comprises at least two fagopyritols, and wherein said method further comprises:

separating one of Fagopyritol A2, Fagopyritol B1, and Fagopyritol B2 from the at least two fagopyritols.

23. A method according to claim 22, wherein said separating one of Fagopyritol A2, Fagopyritol B1, and Fagopyritol B2 from the at least two fagopyritols is carried out chromatographically.

24. A method according to claim 23, wherein said separating one of Fagopyritol A2, Fagopyritol B1, and Fagopyritol B2 from the at least two fagopyritols is carried out on a amine-functionalized silica gel.

25. A method according to claim 23, wherein said separating one of Fagopyritol A2, Fagopyritol B1, and Fagopyritol B2 from the at least two fagopyritols is carried out using an acetonitrile:water eluent.

* * * * *